US008093030B2

(12) United States Patent
Schoenfeld et al.

(10) Patent No.: US 8,093,030 B2
(45) Date of Patent: *Jan. 10, 2012

(54) THERMOSTABLE VIRAL POLYMERASES AND METHODS OF USE

(75) Inventors: Thomas W. Schoenfeld, Madison, WI (US); Vinay K. Dhodda, Madison, WI (US); Robert A. Difrancesco, Waunakee, WI (US); David A. Mead, Middleton, WI (US)

(73) Assignee: Lucigen Corporation, Middleton, WI (US)

(*) Notice: Subject to any disclaimer, the term of this patent is extended or adjusted under 35 U.S.C. 154(b) by 770 days.

This patent is subject to a terminal disclaimer.

(21) Appl. No.: 12/089,221

(22) PCT Filed: Oct. 6, 2006

(86) PCT No.: PCT/US2006/039406
§ 371 (c)(1),
(2), (4) Date: Apr. 4, 2008

(87) PCT Pub. No.: WO2007/044671
PCT Pub. Date: Apr. 19, 2007

(65) Prior Publication Data
US 2008/0268498 A1  Oct. 30, 2008

Related U.S. Application Data

(60) Provisional application No. 60/805,695, filed on Jun. 23, 2006, provisional application No. 60/724,207, filed on Oct. 6, 2005.

(51) Int. Cl.
*C12N 9/12* (2006.01)
*C12P 19/34* (2006.01)

(52) U.S. Cl. ........ 435/194; 435/183; 435/91.1; 530/350

(58) Field of Classification Search .................. None
See application file for complete search history.

(56) References Cited

U.S. PATENT DOCUMENTS

| | | | |
|---|---|---|---|
| 4,748,111 A | 5/1988 | Dattagupta et al. | |
| 4,795,699 A | 1/1989 | Tabor et al. | |
| 4,883,750 A | 11/1989 | Whiteley et al. | |
| 4,965,188 A | 10/1990 | Mullis et al. | |
| 4,994,373 A | 2/1991 | Stavrianopoulos et al. | |
| 5,001,050 A * | 3/1991 | Blanco et al. | 435/5 |
| 5,043,272 A | 8/1991 | Hartley | |
| 5,130,238 A | 7/1992 | Malek et al. | |
| 5,198,543 A | 3/1993 | Blanco et al. | |
| 5,242,794 A | 9/1993 | Whiteley et al. | |
| 5,273,638 A | 12/1993 | Kenrad et al. | |
| 5,328,824 A | 7/1994 | Ward et al. | |
| 5,354,668 A | 10/1994 | Auerbach | |
| 5,409,818 A | 4/1995 | Davey et al. | |
| 5,427,930 A | 6/1995 | Birkenmyer et al. | |
| 5,455,166 A | 10/1995 | Walker | |
| 5,489,523 A * | 2/1996 | Mathur | 435/194 |
| 5,521,065 A | 5/1996 | Whiteley et al. | |
| 5,547,843 A | 8/1996 | Studier et al. | |
| 5,591,609 A | 1/1997 | Auerbach | |
| 5,614,389 A | 3/1997 | Auerbach | |
| 5,614,390 A | 3/1997 | McCaslin et al. | |
| 5,629,158 A | 5/1997 | Uhlen | |
| 5,629,179 A | 5/1997 | Mierendorf et al. | |
| 5,714,320 A | 2/1998 | Kool | |
| 5,733,733 A | 3/1998 | Auerbach | |
| 5,744,312 A * | 4/1998 | Mamone et al. | 435/6 |
| 5,854,033 A | 12/1998 | Lizardi | |
| 6,124,120 A | 9/2000 | Lizardi | |
| 6,143,495 A | 11/2000 | Lizardi et al. | |
| 6,183,960 B1 | 2/2001 | Lizardi | |
| 6,210,884 B1 | 4/2001 | Lizardi | |
| 6,255,082 B1 | 7/2001 | Lizardi | |
| 6,280,949 B1 | 8/2001 | Lizardi | |
| 6,329,150 B1 | 12/2001 | Lizardi et al. | |
| 6,344,329 B1 | 2/2002 | Lizardi | |
| 6,425,434 B1 | 7/2002 | Muller | |
| 6,492,161 B1 | 12/2002 | Hjorleifsdottir et al. | |
| 6,642,034 B2 | 11/2003 | Lizardi | |
| 6,812,018 B2 | 11/2004 | Wicher et al. | |
| 2003/0087392 A1 | 5/2003 | Hjorleifsdottir | |
| 2003/0211494 A1 | 11/2003 | Hreggvidsson | |
| 2004/0209249 A1 | 10/2004 | Aevarsson | |
| 2005/0282155 A1 | 12/2005 | Schoenfeld | |

FOREIGN PATENT DOCUMENTS

| | | |
|---|---|---|
| EP | 0128332 | 12/1984 |
| EP | 0356021 | 2/1990 |
| EP | 0439182 | 7/1991 |
| EP | 0466520 | 1/1992 |
| EP | 0505012 | 9/1992 |
| EP | 0506825 | 10/1992 |

(Continued)

OTHER PUBLICATIONS

Ngo et al., In the Protein Folding Problem and Tertiary Structure Prediction, 1994, Merz et al. (ed.), Birkhauser, Boston, MA, pp. 433 and 492-495.*
Viguera et al., Journal of Molecular Biology, vol. 312, pp. 323-333, 2001.*
H. Guo et al., "Protein Tolerance to Random Amino Acid Change", PNAS 101(25): 9205-9210, Jun. 2004.*
Andraos, N. et al., "The highly processive DNA polymerase of bacteriophage T5: role of the unique amino and carboxy termini," J. Biol. Chem. (2004) 279(48):50609-50618.
Arezi, B. et al., "Amplification efficiency of thermostable DNA polymerases," Anal. Biochem. (2003) 321(2):226-235.
Augustin, M.A. et al., "Progress towards single-molecule sequencing: enzymatic synthesis of nucleotide-specifically labeled DNA," J. Biotechnol. (2001) 86(3):289-301.

(Continued)

*Primary Examiner* — Richard Hutson
(74) *Attorney, Agent, or Firm* — Joseph T. Leone, Esq.; Daniel A. Blasiole; DeWitt Ross & Stevens, S.C.

(57) ABSTRACT

Thermostable viral polymerases exhibiting a combination of activities selected from, proofreading (3'-5') exonuclease activity, nick translating (5'-3') nuclease activity, synthetic primer-initiated polymerase activity, nick-initiated polymerase activity, reverse transcriptase activity, strand displacement activity, and/or decreased discrimination against incorporation of nucleotide analogs. Also provided are compositions including the polymerases, polynucleotides encoding the polymerases and methods of using the polymerases.

43 Claims, 4 Drawing Sheets

FOREIGN PATENT DOCUMENTS

| | | |
|---|---|---|
| EP | 0667393 | 8/1995 |
| JP | 4262799 | 9/1992 |
| JP | 4304900 | 10/1992 |
| WO | WO 91/08307 | 6/1991 |
| WO | WO 92/01813 | 2/1992 |
| WO | WO 94/24312 | 10/1994 |
| WO | WO 95/03430 | 2/1995 |
| WO | WO 95/03432 | 2/1995 |
| WO | WO 95/22623 | 8/1995 |
| WO | WO 95/25180 | 9/1995 |
| WO | WO 95/35390 | 12/1995 |
| WO | WO 97/19193 | 5/1997 |
| WO | WO 97/20948 | 6/1997 |
| WO | WO 97/42346 | 11/1997 |

OTHER PUBLICATIONS

Barnes, W.M., "PCR amplification of up to 35-kb DNA with high fidelity and high yield from lambda bacteriophage templates," Proc. Natl. Acad. Sci. USA (1994) 91(6):2216-2220.

Bebenek, A. et al., "Interacting fidelity defects in the replicative DNA polymerase of bacteriophage RB69," J. Biol. Chem. (2001) 276(13):10387-10397.

Bebenek, K. et al., "Analyzing fidelity of DNA polymerases," Methods Enzymol. (1995) 262:217-232.

Blanco, L. et al., "Terminal protein-primed DNA amplification," Proc. Natl. Acad. Sci. USA (1994) 91(25):12198-12202.

Braithwaite, D.K. et al., "Compilation, alignment, and phylogenetic relationships of DNA polymerases," Nuc. Acids Res. (1993) 21(4):787-802.

Breitbart, M. et al., "Genomic analysis of uncultured marine viral communities," Proc. Natl. Acad. Sci USA (2002) 99:14250-14255.

Breitbart, M. et al., "Phage community dynamics in hot springs," Appl. Environ. Microbiol. (2004) 70:1633-1640.

Canceill, D. et al., "Replication slippage of different DNA polymerases is inversely related to their strand displacement efficiency," J. Biol. Chem. (1999) 274(39):27481-27490.

Chen, F. et al., "Genetic diversity in marine algal virus communities as revealed by sequence analysis of DNA polymerase genes," Appl. Environ. Microbiol. (1996) 62(8):2869-2874.

Craggs, J.K. et al., "Development of a strand-specific RT-PCR based assay to detect the replicative form of hepatitis C virus RNA," J. Virol. Meth. (2001) 94:111-120.

Dean, F.B. et al., "Rapid amplification of plasmid and phage DNA using Phi29 DNA polymerase and multiply-primed rolling circle amplification," Gen. Res. (2001) 1095-1099.

Fuhrman, J.A., "Marine viruses and their biogeochemical and ecological effects," Nature (1999) 399(6736):541-548.

Gardner, A.F. et al., "Comparative kinetics of nucleotide analog incorporation by vent DNA polymerase," J. Biol. Chem. (2004) 279(12):11834-11842.

Gharizadeh, B. et al., "Improvements in pyrosequencing technology by employing sequenase polymerase," Anal. Biochem. (2004) 330(2):272-280.

Hogrefe, H.H. et al., "DNA polymerases from hyperthermophiles," Meth. Enzym. (2001) 334:91-116.

Hosono, S. et al., "Unbiased whole-genome amplification directly from clinical samples," Gen. Res. (2003) 13:954-964.

Huber, H.E. et al., "*Escherichia coli* thioredoxin stabilizes complexes of bacteriophage T7 DNA polymerase and primed templates," J. Biol. Chem. (1987) 262(33):16224-16232.

Ishino, Y. et al., "A novel DNA polymerase family found in archaea," J. Bact. (1998) 180(8):2232-2236.

Karlin, S. et al., "Methods for assessing the statistical significance of molecular sequence features by using general scoring schemes," Proc. Natl. Acad. Sci. USA (1990) 87:2264-2268.

Karlin, S. et al., "Applications and statistics for multiple high-scoring segments in moecular sequences," Proc. Natl. Acad. Sci. USA (1993) 90:5873-5877.

Kling, J., "Ultrafast DNA sequencing," Nat. Biotechnol. (2003) 21(12):1425-1427.

Kong, H. et al., "Characterization of a DNA polymerase from the hyperthermophile archaea thermococcus litoralis. Vent DNA polymerase, steady state kinetics, thermal stability, processivity, strand displacement, and exonuclease activities," J. Biol. Chem. (1993) 268(3):1965-1975.

Li, Y. et al., "Structure-based design of Taq DNA polymerases with improved properties of dideoxynucleotide incorporation," Proc. Natl. Acad. Sci. USA 1999) 96(17):9491-9496.

Lu, L. et al., "A refined long RT-PCR technique to amplify complete viral RNA genome sequences from clinical samples: application to a novel hepatitis C virus variant of genotype 6," J. Virol. Meth. (2005) 126:139-148.

Lutz, S. et al., "An in vitro screening technique for DNA polymerases that can incorporate modified nucleotides. Pseudo-thymidine as a substrate for thermostable polymerases," Nuc. Acids Res. (1999) 27(13):2792-2798.

Meijer, W.J. et al., "Phi29 family of phages," Microbiol. Mol. Biol. Rev. (2001) 65(2):261-287.

Metzker, M.L. et al., "Termination of DNA synthesis by novel 3'-modified-deoxyribonucleoside 5'-triphosphates," Nuc. Acids Res. (1994) 22:4259-4267.

Mitra, R.D. et al., "Fluorescent in situ sequencing on polymerase colonies," Anal. Biochem. (2003) 320(1):55-65.

Motz, M. et al., "Sequential DEXAS: A method for obtaining DNA sequences from genomic DNA and blood in one reaction," Nuc. Acids Res. (2003) 31(20):e121 (8 pages).

Mytelka, D.S. et al., "Analysis and suppression of DNA polymerase pauses associated with a trinucleotide consensus," Nuc. Acids Res. (1996) 24(14):2774-2781.

Ohno, K. et al,. "Direct DNA sequencing from colony: analysis of multiple deletions of mitochondrial genome," Biochim. Biophys. Acta (1991) 1090(1):9-16.

Paez, J.G. et al., "Genome coverage and sequence fidelity of Φ29 polymerase-based multiple strand displacement whole genome amplification," Nuc. Acids Res. (2004) 32(9):e71 (11 pages).

Patel, P.H. et al., "Prokaryotic DNA polymerase I: evolution, structure, and 'base flipping' mechanism for nucleotide selection," J. Mol. Biol. (2001) 308:823-837.

Patel, S.S. et al., "Pre-steady-state kinetic analysis of processive DNA replication including complete characterization of an exonuclease-deficient mutant," Biochem. (1991) 30(2):511-525.

Perler, F.B. et al., "Thermostable DNA polymerases," Adv. Protein Chem. (1996) 48:377-435.

Peterson, M.G., "DNA sequencing using Taq polymerase," Nuc. Acids Res. (1988) 16(22):10915.

Reeve, M.A. et al., "A novel thermostable polymerase for DNA sequencing," Nature (1995) 376:796-797.

Ronaghi, M. et al., "PCR-introduced loop structure as primer in DNA sequencing," Biotechniques (1998) 25(5):876-884.

Rondon, M.R. et al., "The Earth's bounty: assessing and accessing soil microbial diversity," Trends Biotechnol. (1999) 17(10):403-409.

Sakaiu, Y. et al., "Isolation and characterization of a bacteriophage infectious to an extreme thermophile, Thermus thermophilus HB8," J. Virol. (1975) 15(6):1449-1453.

Sanger, F. et al., "A rapid method for determining sequences in DNA by primer synthesis with DNA polymerase," J. Mol. Biol. (1975) 94(3):441-448.

Saturno, J. et al., "A novel kinetic analysis to calculate nucleotide affinity of proofreading DNA polymerases. Application to phi 29 DNA polymerase fidelity mutants," J. Biol. Chem. (1995) 270(52):31235-31243.

Shendure, J. et al., "Advanced sequencing technologies: methods and goals," Nat. Rev. Genet. (2004) 5(5):335-344.

Skerra, A., "Phosphorothioate primers improve the amplification of DNA sequences by DNA polymerases with proofreading activity," Nucl. Acids Res. (1992) 20(14):3551-3554.

Slatko, B.E., "Thermal cycle dideoxy DNA sequencing," Methods Mol. Biol. (1994) 31:35-45.

Slatko, B.E., "Thermal cycle dideoxy DNA sequencing," Mol. Biotechnol. (1996) 6(3):311-322.

Smith, L.M. et al, "Fluorescence detection in automated DNA sequence analysis," Nature (1986) 321(6071):674-679.

Southworth, M.W. et al., "Cloning of thermostable DNA polymerases from hyperthermophilic marine archaea with emphasis on thermococcus sp. 9 degrees N-7 and mutations affecting 3'-5' exonuclease activity," Proc. Natl. Scad. Sci. USA (1996) 93(11):5281-5285.

Spurgeon, S.L. et al., "New DNA Sequencing Enzymes, in DNA Sequencing: Optimizing the Process and Analysis," Kieleczawa, J. editor, Jones and Bartlett Publishers, Boston (2005) p. 35-54.

Stetter, K.O., "Hyperthermophiles: isolation, classification and properties," in Extremophiles: Microbial Life in Extreme Environments, Horikoshi and Grant, Wiley-Liss, New York (1998) Chapter 1, pp. 1-24.

Steward, G.B. et al., "Genome size distributions indicate variability and similaries among marine viral assemblages from diverse environments," Limnol. Oceanogr. (2000) 45(8):1697-1706.

Syvanen, A.C., "From gels to chips: 'minisequencing' primer extension for analysis of point mutations and single nucleotide polymorphisms," Human. Mutat (1999) 13(1):1-10.

Tabor, S. et al., "A single residue in DNA polymerases of the *Escherichia coli* DNA polymerase I family is critical for distinguishing between deoxy- and dideoxyribonucleotides," Proc. Natl. Acad. Sci. USA (1995) 92(14):6339-6343.

Tabor, S. et al., "DNA sequence analysis with a modified bacteriophage T7 DNA polymerase," Proc. Natl. Acad. Sci. USA (1987b):84(14):4767-4771.

Tabor, S. et al., "*Escherichia coli* thioredoxin confers processivity on the DNA polymerase activity of the gene 5 protein of bacteriophage T7," J. Biol. Chem. (1987a):262(33):16212-16223.

Tindall, K.R. et al., "Fidelity of DNA synthesis by the thermus aquaticus DNA polymerase," Biochem. (1988) 27(16):6008-6013.

Van Den Boom, D. et al., "Combined amplification and sequencing in a single reaction using two DNA polymerases with differential incorporation rates for dideoxynucleotides," J. Biochem. Biophys. Methods. (1997) 35(2):69-79.

Vander Horn, P.B. et al., "Thermo sequenase DNA polymerase and T. acidophilum pyrophosphatase: new thermostable enzymes for DNA sequencing," Biotechniques (1997) 22(4):758-765.

Viguera, E. et al., "In vitro replication slippage by DNA polymerases from thermophilic organisms," J. Mol. Biol. (2001) 312:323-333.

Villarreal, L.P. et al., "A hypothesis for DNA viruses as the origin of eukaryotic replication proteins," J. Virol. (2000) 74(15):7079-7084.

Wommack, K.E. et al., "Virioplankton: viruses in aquatic ecosystems," Microbiol. Mol. Biol. Rev. (2000) 64(1):69-114.

Zillig, W. et al., "Viruses, plasmids and other genetic elements of thermophilic and hyperthermophilic archaea," FEMS Mic. Microbiol. Rev. (1996) 18(2-3):225-236.

International Search Report and Written Opinion for Application No. PCT/US2006/039406 dated May 7, 2007 (11 pages).

* cited by examiner

THERMOSTABLE VIRAL POLYMERASES AND METHODS OF USE

This application is a national stage filing under 35 U.S.C. 371 of International Application No. PCT/US2006/039406, filed on Oct. 6, 2006, which claims benefit of priority under 35 U.S.C. §119 from U.S. Provisional Application Ser. No. 60/724,207, filed Oct. 6, 2005, and U.S. Provisional Application Ser. No. 60/805,695, filed Jun. 23, 2006. Each application is incorporated herein by reference in its entirety.

STATEMENT REGARDING FEDERALLY SPONSORED RESEARCH

This invention was made with United States government support awarded by the National Science Foundation (Grant Nos. 0109756 and 0215988) and the National Institutes of Health (Grant No. R43 HG002714-01). The United States has certain rights in this invention.

NAMES OF PARTIES TO A JOINT RESEARCH AGREEMENT

Not applicable.

REFERENCE TO A SEQUENCE LISTING

This application includes a sequence listing, submitted herewith as an Appendix and on one (1) computer readable disc. The content of the sequence listing is incorporated herein by reference in its entirety.

INTRODUCTION

There are seven known families of DNA polymerases, including A, B, C, D, X, Y and RT. The most widely used DNA polymerases are family A and B polymerases, especially those that are stable to greater than 90° C. and are active at temperatures of a least 70° C., conditions commonly used in DNA detection and analysis methods, e.g., polymerase chain reaction or thermocycled DNA sequencing. These DNA polymerases are referred to as "thermostable" DNA polymerases.

Thermostable DNA polymerases are commonly used in recombinant DNA technology to generate polynucleotide sequences from both known and unknown target sequences. It is appreciated that the biochemical attributes of a given enzyme may either enhance or limit its usefulness, depending upon the particular reaction conditions and desired functions. Characteristics that are generally considered to affect the utility of thermostable polymerases include strand displacement activity, processivity, both 3'-5' and 5'-3' exonuclease activity, affinity for template DNA and for nucleotides (both canonical and modified), error rate and degree of thermostability. Despite extensive investigation to discover new polymerases and attempts to manipulate buffer formulations to optimize polymerase activity, there remains a need for thermostable DNA polymerases having an appropriate combination of the above attributes for particular applications.

Many bacterial and archaeal thermostable DNA polymerases are known and used, including Taq, VENT$_R$ and Bst. Each of these enzymes, while effective for use in particular applications, has limitations. For example, both Bst and Taq lack proofreading activity and, therefore, have a relatively high error rate. Extensive efforts to isolate new thermostable DNA polymerases have provided dozens of alternative enzymes, but only modest improvements in biochemical properties have resulted.

Viral DNA polymerases (including phage polymerase), like their bacterial counterparts, catalyze template-dependent synthesis of DNA. However, viral polymerases differ significantly in their biochemical characteristics from the bacterial polymerases currently used for most DNA and RNA analysis. For example, T5, T7 and phi29 DNA polymerases are among the most processive enzymes known. RB49 DNA polymerase, in addition to a highly active proofreading function, has the highest known fidelity of initial incorporation. T7 and phi29 DNA polymerases have the lowest measured replication slippage due to high processivity. T7 DNA polymerase can efficiently incorporate dideoxynucleotides, thereby enabling facile chain terminating DNA sequence analysis. The viral reverse transcriptases are unique among reagents in their efficiency in synthesizing a DNA product using an RNA template.

Despite their advantages, deficiencies among the available viral enzymes are apparent. Notably, there is no thermostable viral polymerase widely available. U.S. Patent Publication US 2003/0087392 describes a moderately thermostable polymerase isolated from bacteriophage RM378. Although this polymerase is described as "expected to be much more thermostable than of bacteriophage T4," and is said to lack both 3'-5' and 5'-3' exonuclease activities, RM378 polymerase is not thermostable enough for thermocycled amplification or sequencing. A larger pool of potential viral reagent DNA polymerases is needed for use in DNA detection and analysis methods.

SUMMARY

The invention pertains generally to polymerases suitable for use as reagent enzymes. Because the polymerases described herein were isolated from thermophilic viruses, they are significantly more thermostable than those of other (e.g. mesophilic) viruses, such as the T4 bacteriophage of *Escherichia coli*. The enhanced stability of the polymerases described herein permits their use under temperature conditions which would be prohibitive for other enzymes and increasing the range of conditions which can be employed, thereby improving amplification specificity and providing a thermostable viral enzyme that can be used in thermocycling.

Accordingly, one aspect of the invention provides a substantially purified polymerase having an amino acid sequence comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or sequence variants thereof.

One aspect of the invention also provides a substantially purified polymerase that demonstrates nick-initiated polymerase activity, primer-initiated polymerase activity, 3'-5' exonuclease (proofreading) activity, reverse transcriptase activity and/or strand displacement activity. In some embodiments of the invention, the purified polymerases lack 3'-5' exonuclease activity. Other polymerases of the invention do not discriminate against nucleotide analog incorporation.

Other aspects of the invention provide isolated polynucleotides encoding the polymerases, polynucleotide constructs comprising the polynucleotides, recombinant host cells comprising the polynucleotide constructs and methods of producing thermostable polymerases.

In another aspect, the invention provides a method of synthesizing a DNA copy or complement of a polynucleotide template. The method includes contacting the template with a polypeptide of the invention under conditions sufficient to promote synthesis of the copy or complement. In some embodiments, the template is RNA, and in other embodiments, the template is DNA.

Other aspects of the invention will become apparent by consideration of the detailed description of several embodiments and from the claims.

DETAILED DESCRIPTION OF SEVERAL EMBODIMENTS

Figure 1:
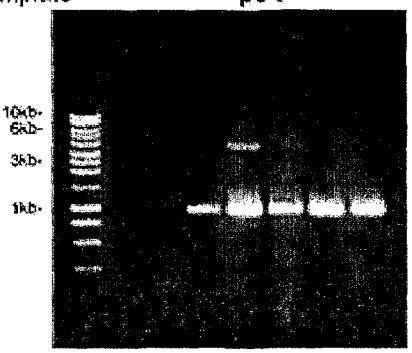
FIG. 1 is a photographic image of an electrophoretic gel showing results of polymerase chain reaction (PCR) amplification of a 1 kb pUC19 sequence using a polymerase of the invention and two commercially available polymerases.

Before any embodiments of the invention are explained in detail, it is to be understood that the invention is not limited in its application to the details of construction and the arrangement of components set forth in the following description or illustrated in the following figures and examples. The invention is capable of other embodiments and of being practiced or of being carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional items.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

The invention relates to polymerases, polynucleotides and constructs encoding the polymerases, and methods for using the polymerases. The polymerases of the invention are suitable for sequence-specific methods including PCR, as well as whole genome nucleic acid amplification. As will be appreciated, the polymerases described herein are useful in any research or commercial context wherein polymerases typically are used for DNA analysis, detection, or amplification.

As used herein, "polymerase" refers to an enzyme with polymerase activity that may or may not demonstrate further activities, including, but not limited to, nick-initiated polymerase activity, primer-initiated polymerase activity, 3'-5' exonuclease (proofreading) activity, reverse transcriptase activity and/or strand displacement activity. Polymerases of the invention suitably exhibit one or more activities selected from polymerase activity, proofreading (3'-5') exonuclease activity, nick translating (5'-3') nuclease activity, primer-initiated polymerase activity, reverse transcriptase activity, strand displacement activity, and/or increased propensity to incorporate chain terminating analogs. As will be appreciated by the skilled artisan, an appropriate polymerase may be selected from those described herein based on any of these and other activities or combinations thereof, depending on the application of interest.

The polymerases described herein are of viral origin. For purposes of this description, a "virus" is a nucleoprotein entity which depends on host cells for the production of progeny. The term encompasses viruses that infect eukaryotic, bacterial or archaeal hosts, and may be used interchangeably with "bacteriophage," "archaeaphage" or "phage," depending on the host.

The purified polymerases of the invention were compared to known polymerases and found to have one or more enzymatic domains conserved. The enzymatic domains and other domains (e.g., signal peptide, linker domains, etc.) can be readily identified by analysis and comparison of the sequence of the viral polymerases with sequences of other polymerases using publicly available comparison programs, such as ClustalW (European Bioinformatics Institute).

The polymerases of the invention are substantially purified polypeptides. As used herein, the term "purified" refers to material that is at least partially separated from components which normally accompany it in its native state. Purity of polypeptides is typically determined using analytical techniques such as polyacrylamide gel electrophoresis or high performance liquid chromatography. A polypeptide that is the predominant species present in a preparation is "substantially purified." The term "purified" denotes that a preparation containing the polypeptide may give rise to essentially one band in an electrophoretic gel. Suitably, polymerases of the invention are at least about 85% pure, more suitably at least about 95% pure, and most suitably at least about 99% pure.

The polymerases of the invention are thermostable. The term "thermostable" is used herein to refer to a polymerase that retains at least a portion of one activity after incubation at relatively high temperatures, i.e., 50-100° C. In some cases, thermostable enzymes exhibit optimal activity at relatively high temperatures, i.e., about 50-100° C. In some embodiments, the thermostable polymerases exhibit optimal activity from about 60° C. to 70° C. Most suitably, thermostable enzymes are capable of maintaining at least a portion of at least one activity after repeated exposure to temperatures from about 90° C. to about 98° C. for up to several minutes for each exposure.

The polymerases of the invention have amino acid sequences comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, or may be sequence variants thereof, i.e., variants of any of the previously listed sequences. The term "sequence variants" refers to polymerases that retain at least one activity and have at least about 80% identity, more suitably at least about 85% identity, more suitably at least about 90% identity, more suitably at least about 95% identity, and most suitably at least about 98% or 99% identity, to the amino acid sequences provided. Percent identity may be determined using the algorithm of Karlin and Altschul (Proc. Natl. Acad. Sci. 87: 2264-68 (1990), modified Proc. Natl. Acad. Sci. 90: 5873-77 (1993). Such algorithm is incorporated into the BLASTx program, which may be used to obtain amino acid sequences homologous to a reference polypeptide, as is known in the art.

The term "sequence variants" may also be used to refer to thermostable polymerases having amino acid sequences including conservative amino acid substitutions. Such substitutions are well known in the art. The term "sequence variants" also refers to polymerases that are subjected to site-directed mutagenesis wherein one or more substitutions, additions or deletions may be introduced, e.g., as described below, to provide altered functionality, as desired.

In one particularly suitable embodiment, a polymerase of the invention includes the sequence of amino acids shown in SEQ ID NO:6. This polymerase is also referred to herein as "polymerase 3173." In other embodiments, polymerases of the invention include mutated forms of polymerase 3173, including those having sequences shown in SEQ ID NOS:25-27. The mutated forms of polymerase 3173 suitably exhibit strand displacement activity, substantially reduced exonuclease activity, reduced discrimination for nucleotide analogs, or combinations thereof, as further described below. Suitably, polymerase 3173 has a higher fidelity as compared to commercially available polymerases, e.g., $VENT_R$ (New England Biolabs).

Polymerase activity may be determined by any method known in the art. Determination of activity may be based on, e.g., the activity of extending a primer on a template. For example, a labeled synthetic primer may be annealed to a template which extends several nucleotides beyond the 3' end of the labeled primer. After incubation in the presence of DNA polymerase, deoxynucleotide triphosphates, a divalent cation such as magnesium and a buffer to maintain pH at neutral or slightly alkaline, and necessary salts, the labeled primer may be resolved by, e.g., capillary electrophoresis, and detected. DNA polymerase activity may then be detected as a mobility shift of the labeled primer corresponding to an extension of the primer.

In some embodiments, polymerases of the invention may substantially lack 3'-5' exonuclease activity. Suitable polymerases substantially lacking 3'-5' exonuclease activity are shown in SEQ ID NOS: 4, 8, and 14. In some embodiments, the polymerases may be subjected to site-directed mutagenesis, i.e., substitutions, additions or deletions may be introduced, to reduce or eliminate the 3'-5' exonuclease activity of the native polypeptide. Suitable mutations include those which replace charged amino acids with neutral amino acids in the exonuclease domain of the polymerase. For example, with respect to the polymerase of SEQ ID NO:6, mutations are suitably introduced in the region encompassing amino acid residue 30 to residue 190 of the native polypeptide. Suitably, one or more acidic amino acids (e.g., aspartate or glutamate) in this region are replaced with aliphatic amino acids (e.g., alanine, valine, leucine or isoleucine). Suitably, the aspartate at position 49 and/or the glutamate at position 51 of SEQ ID NO:6 is substituted. Suitably, one or both of these residues are substituted with alanine. Exemplary polymerases subjected to mutagenesis and having substantially reduced 3'-5' exonuclease activity are shown in SEQ ID NOS: 25, 26, and 27.

Determination of whether a polypeptide exhibits exonuclease activity, or in some embodiments, exhibits substantially reduced exonuclease activity, may be readily determined by standard methods. For example, polynucleotides can be synthesized such that a detectable proportion of the nucleotides are radioactively labeled. These polynucleotides are incubated in an appropriate buffer in the presence of the polypeptide to be tested. After incubation, the polynucleotide is precipitated and exonuclease activity is detectable as radioactive counts due to free nucleotides in the supernatant.

Some polymerases of the invention, e.g., polymerase 3173 and sequence variants thereof, exhibit nick-initiated polymerase activity. As used herein, "nick-initiated polymerase activity" refers to polymerase activity in the absence of exogenous primers which is initiated by single-strand breaks in the template. In these embodiments, synthesis initiates at single-strand break in the DNA, rather than at the terminus of an exogenous synthetic primer. As will be appreciated, with nick-initiated synthesis, removal of primers is unnecessary, reducing cost, handling time and potential for loss or degradation of the product. In addition, nick-initiated synthesis reduces false amplification signals caused by self-extension of primers. Nick-initiated polymerase activity is particularly suitable for "sequence-independent" synthesis of polynucleotides. As used herein, the term "sequence-independent amplification" is used interchangeably with "whole genome amplification," and refers to a general amplification of all the polynucleotides in a sample. As is appreciated by those of skill in the art, the term "whole genome amplification" refers to any general amplification method whether or not the amplified DNA in fact represents a "genome," for example, amplification of a plasmid or other episomal element within a sample. Suitably, nick-initiated polymerase activity can be detected, e.g., on an agarose gel, as an increase in the amount of DNA product due to synthesis in the presence of a nicking enzyme as compared to minimal or no product synthesized when nicking enzyme is absent from the reaction.

In some embodiments, the polymerases of the invention exhibit primer-initiated polymerase activity, and are suitable for sequence-dependent synthesis of polynucleotides. "Sequence-dependent synthesis" or "sequence-dependent amplification" refers to amplification of a target sequence relative to non-target sequences present in a sample. The most commonly used technique for sequence-dependent synthesis of polynucleotides is the polymerase chain reaction (PCR). The sequence that is amplified is defined by the inclusion in the reaction of two synthetic oligonucleotides, or "primers," to direct synthesis to the polynucleotide sequence intervening between the cognate sequences of the synthetic primers.

Thermocycling is utilized to allow exponential amplification of the sequence. As used herein, sequence-dependent amplification is referred to herein as "primer-initiated." As is appreciated by those of skill in the art, primers may be designed to amplify a particular template sequence, or random primers are suitably used, e.g., to amplify a whole genome. Exemplary polymerases exhibiting primer-initiated polymerase activity have amino acid sequences comprising SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, or sequence variants thereof.

In some embodiments, the polypeptides of the invention suitably exhibit reverse transcriptase activity, as exemplified below. "Reverse transcriptase activity" refers to the ability of a polymerase to produce a complementary DNA (cDNA) product from an RNA template. Typically, cDNA is produced from RNA in a modification of PCR, referred to as reverse transcription PCR, or RT-PCR. In contrast to retroviral reverse transcriptases, e.g., those of Moloney Moloney Murine Leukemia Virus or Avian Myeloblastosis Virus, the present polymerases may be useful for both reverse transcription and amplification, simplifying the reaction scheme and facilitating quantitative RT-PCR. In contrast to bacterial DNA polymerases, e.g., that of *Thermus thermophilus*, inclusion of manganese in the RT-PCR reaction buffer is not required using some embodiments of the invention. As is appreciated, manganese may cause a substantial reduction in fidelity. Exemplary polymerases exhibiting reverse transcriptase activity have amino acid sequences comprising SEQ ID NO:6, SEQ ID NO:25, SEQ ID NO:26, SEQ ID NO:27 or sequence variants thereof.

The polypeptides of the invention suitably exhibit strand displacement activity. As used herein, "strand displacement activity" refers to the ability of a polymerase to displace downstream DNA encountered during synthesis. Protocols such as, e.g., strand displacement amplification (SDA) may exploit this activity. Strand displacement activity may be determined using primer-initiated synthesis. A polymerase of the invention is incubated in the presence of a plasmid and random primers. A polymerase of the invention may extend the primer the complete circumference of the plasmid at which point the 5' end of the primer is encountered. If the polymerase is capable of strand displacement activity, the nascent strand of DNA is displaced and the polymerase continues DNA synthesis. The presence of strand displacement activity results in a product having a molecular weight greater than the original template. The higher molecular weight product can be easily detected by agarose gel electrophoresis. Suitable polymerases exhibiting strand displacement activity have amino acid sequences comprising SEQ ID NO:6, SEQ ID NO:25, SEQ ID NO:26, SEQ ID NO:27 and sequence variants thereof.

In some embodiments, the invention provides purified polymerases that have the ability to incorporate nucleotide analogs, i.e., polymerases that do not discriminate, or exhibit reduced discrimination, against incorporation of nucleotide analogs. Nucleotide analogs may include chain terminating analogs including acyNTPs, ddNTPs, analogs that have moieties that allow facile detection, including fluorescently labeled nucleotides, e.g., fluorescein or rhodamine derivatives, and/or combinations of chain terminators with detectable moieties, e.g., dye terminators. Nucleotide analogs may also have alternative backbone chemistries, e.g., O-methyl or 2'azido linkages, alternative ring chemistries, and/or ribonucleotide acids rather than deoxyribonucleotides.

Discrimination of a polymerase for nucleotide analogs can be measured by, e.g., determining kinetics of the incorporation reaction, i.e., the rate of phosphoryl transfer and/or binding affinity for nucleotide analog. Suitably, a polymerase of the invention may have a relative incorporation efficiency of nucleotide analogs that is at least 10% of the incorporation efficiency of deoxynucleotides, i.e., in a reaction including a polymerase of the invention and equimolar amounts of nucleotide analogs and corresponding standard deoxynucleotides, the polymerase is 90% more likely to incorporate the deoxynucleotide. It is appreciated that this embodiment will be particularly suitable for use in sequencing applications, as well as detecting single nucleotide polymorphisms. In other embodiments, the incorporation of nucleotide analogs may aid in the detection of specific sequences by hybridization, e.g., in microarrays, by altering nuclease susceptibility, hybridization strength, selectivity or chemical functionality of a synthetic polynucleotide. Suitably, polymerases of the invention have a relative incorporation efficiency of nucleotide analogs at least about 10% of the incorporation efficiency of standard deoxynucleotides, more suitably at least about 20% incorporation efficiency of standard deoxynucleotides, more suitably at least about 50% incorporation efficiency of standard deoxynucleotides, more suitably at least about 75% incorporation efficiency of standard deoxynucleotides still more suitably at least about 90% incorporation efficiency of standard deoxynucleotides and most suitably at least about 98-99% incorporation efficiency of standard deoxynucleotides.

Suitable polymerases capable of incorporating nucleotide analogs include sequence variants of the polymerases described herein, wherein the polymerase is mutated in the dNTP binding domain to reduce discrimination against chain terminating analogs. As is known in the art, the dNTP binding domain of most polymerases may be characterized as having the sequence $KN_1, N_2 N_3 N_4 N_5 N_6 N_7 YG/Q$, wherein $N_1$-$N_7$ are independently any amino acid and $N_7$ may or may not be present, depending on the polymerase. Most suitably, a substitution is introduced at $N_4$ of the dNTP binding domain. Most suitably, the amino acid at position $N_4$ is substituted to tyrosine or a functionally equivalent amino acid that may be chosen by routine experimentation. As an example, a substitution may be made at an amino acid position corresponding to amino acid position 418 of polymerase 3173. Suitably, the phenylalanine natively present at position 418 of polymerase 3173 is replaced with tyrosine ("F418Y"). Most suitably, the polymerases exhibit substantially reduced discrimination between chain terminating nucleotides (e.g., nucleotide analogs) and their native counterparts, as shown in the examples. In some cases, a polymerase of the invention discriminates 50 fold less, or 100 fold less, or 500 fold less, or 1000 fold less than its native counterpart.

In other embodiments, the polymerase is a double mutant. Suitably, the native polypeptide of SEQ ID NO:6 may have one mutation in the region encompassing amino acid residue 30 to residue 190 of the native polypeptide sequence and a second mutation at amino acid position 418. Suitably, the double mutant exhibits both reduced exonuclease activity, as described above, and reduced discrimination for incorporation of nucleotide analogs. One example of a double mutant of polymerase 3173 has both a D49A and a F418Y mutation, and its sequence is shown in SEQ ID NO:27.

The invention further provides compositions including polymerases of the invention. In some embodiments, compositions of the invention include one or more polymerases selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:25, SEQ ID NO:26, SEQ ID NO:27 and sequence variants thereof. In a particular embodiment, the composition comprises SEQ ID NO:6 and one or more polymerases selected from SEQ ID NO:25, SEQ ID NO:26, SEQ ID NO:27 and sequence variants thereof. In other embodiments, polymerases of the invention can be included in a composition with other commercially available polymerases.

Some embodiments of the invention provide isolated polynucleotides encoding the polymerases. The term "isolated polynucleotide" is inclusive of, for example: (a) a polynucleotide which includes a coding sequence of a portion of a naturally occurring genomic DNA molecule that is not flanked by coding sequences that flank that portion of the DNA in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; and (c) a cDNA molecule, a genomic fragment, a fragment produced by polymerase chain reaction, or a restriction fragment. A "vector" is any polynucleotide entity capable of being replicated by standard cloning techniques.

Suitable polynucleotides encoding a polymerase of the invention have the nucleotide sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 or SEQ ID NO:19.

The invention also provides DNA constructs useful in preparing the polypeptides of the invention. The DNA constructs include at least one polynucleotide encoding the polypeptides described herein, operably connected to a promoter. The promoter may be natively associated with the coding sequence, or may be heterologous. Suitable promoters are constitutive and inducible promoters. A "constitutive" promoter is a promoter that is active under most environmental and developmental conditions. An "inducible" promoter is a promoter that is under environmental or developmental regulation. The term "operably connected" refers to a functional linkage between a promoter and a second nucleic acid sequence, wherein the promoter directs transcription of the nucleic acid corresponding to the second sequence. The constructs may suitably be introduced into host cells, such as E. coli or other suitable hosts known in the art, for producing polymerases of the invention. Expression systems are well known in the art.

The present invention further provides a method of synthesizing a copy or complement of a polynucleotide template. The method includes a step of contacting the template with a polypeptide of the invention under conditions sufficient to promote synthesis of the copy or complement. In some embodiments, the template is RNA. In other embodiments, the template is DNA.

A copy or complement of a polynucleotide template may be synthesized using a polymerase of the invention in a thermocycled reaction, e.g., PCR, RT-PCR, or alternatively, using substantially isothermal conditions. As used herein, "substantially isothermal" refers to conditions that do not include thermocycling. Due to their thermostability, the present polypeptides may prove particularly useful in, e.g., strand-displacement amplification (SDA), loop-mediated isothermal amplification (LAMP), rolling circle amplification (RCA) and/or multiple displacement amplification (MDA). Using these techniques, nucleic acids from clinical isolates containing human cells can be amplified for genotyping. Nucleic acids from clinical isolates containing viruses or bacterial cells can be amplified for pathogen detection. Nucleic acids from microbial cells, which may be very difficult to isolate in large quantities, may be amplified for gene mining or enzyme or therapeutic protein discovery.

In some methods of the invention, amplification is carried out in the presence of at least one primer pair, e.g., to amplify a defined target sequence. In other embodiments, random primers are added to promote sequence-independent amplification. In still further embodiments, primers are excluded, and a nick-inducing agent is optionally added to facilitate polymerase activity. A "nick-inducing agent" is defined herein as any enzymatic or chemical reagent or physical treatment that introduces breaks in the phosphodiester bond between two adjacent nucleotides in one strand of a double-stranded nucleic acid. The nicks may be introduced at defined locations, suitably by using enzymes that nick at a recognition sequence, or may be introduced randomly in a target polynucleotide. Examples of nick-inducing enzymes include Nb.Bpu10I (Fermentas Life Sciences), Nt.BstNB I, Nt.Alw I, Nb.BbvC I, Nt.BbvC I, Nb.Bsm I, Nb.BsrD (New England Biolabs) and E. coli endonuclease I.

Due to their unique biochemical properties, the polymerases of the present invention may be particularly suitable for amplifying sequences that are traditionally difficult to amplify. These sequences are referred to herein as "amplification-resistant sequences." For example, some difficult sequences have inverted repeats in their sequences that promote the formation of DNA secondary structure. Others have direct repeats that cause the nascent strand to spuriously re-anneal and cause incorrect insertion or deletion of nucleotides. In other cases, amplification-resistant sequences have a high content of guanine and cytosine (G+C) or, conversely, a high content of adenine and thymidine (A+T) residues. A sequence has a high content of G+C or A+T when at least about 65% of the sequence comprises those residues. In some embodiments, a sequence is considered amplification-resistant when the desired product is at least about 2 kb. In some cases, polymerases of the invention can amplify sequences that are larger than the normal range of PCR, i.e., around 10 kb, as exemplified below.

The polymerases of the invention may be characterized by their thermostability, temperature optimum, fidelity of incorporation of nucleotides, cofactor requirements, template requirements, reaction rate, affinity for template, affinity for natural nucleotides, affinity for synthetic nucleotide analogs and/or activity in various pHs, salt concentrations and other buffer components. As will be appreciated by the skilled artisan, an appropriate polymerase, or combination of polymerases, may be selected based on any of these characteristics or combinations thereof, depending on the application of interest.

The following examples are provided to assist in a further understanding of the invention. The particular materials and conditions employed are intended to be further illustrative of the invention and are not limiting upon the reasonable scope of the appended claims.

EXAMPLES

Example 1

Isolation of Uncultured Viral Particles from a Thermal Spring

Viral particles were isolated from a thermal spring in the White Creek Group of the Lower Geyser Basin of Yellowstone National Park (N 44.53416, W 110.79812; temperature 80° C., pH 8), commonly known as Octopus Spring. Thermal water was filtered using a 100 kiloDalton molecular weight cut-off (mwco) tangential flow filter (A/G Technology, Amersham Biosciences) at the rate of 7 liters per minute for over 90 minutes (630 liters overall), and viruses and microbes were concentrated to 2 liters. The resulting concentrate was filtered through a 0.2 µm tangential flow filter to remove microbial cells. The viral fraction was further concentrated to 100 ml using a 100 kD tangential flow filter. Of the 100 ml viral concentrate, 40 ml was processed further. Viruses were further concentrated to 400 µl and transferred to SM buffer (0.1 M NaCl, 8 mM MgSO4, 50 mM Tris HCl 7.5) by filtration in a 30 kD mwco spin filter (Centricon, Millipore).

Example 2

Isolation of Viral DNA

*Serratia marcescens* endonuclease (Sigma, 10 U) was added to the viral preparation described in Example 1 to remove non-encapsidated (non-viral) DNA. The reaction was incubated for 30 min. at 23° C. Subsequently, EDTA (20 mM) and sodium dodecyl sulfate (SDS) (0.5%) was added. To isolate viral DNA, Proteinase K (100 U) was added and the reaction was incubated for 3 hours at 56° C. Sodium chloride (0.7M) and cetyltrimethylammonium bromide (CTAB) (1%) were added. The DNA was extracted once with chloroform, once with phenol, once with a phenol:chloroform (1:1) mixture and again with chloroform. The DNA was precipitated with 1 ml of ethanol and washed with 70% ethanol. The yield of DNA was 20 nanograms.

Example 3

Construction of a Viral DNA Library

Ten nanograms of viral DNA isolated as described in Example 2 was physically sheared to between 2 and 4 kilobases (kb) using a HydroShear Device (Gene Machines). These fragments were ligated to double-stranded linkers having the nucleotide sequences shown in SEQ ID NOS:21 and 22 using standard methods. The ligation mix was separated by agarose gel electrophoresis and fragments in the size range of 2-4 kb were isolated. These fragments were amplified by standard PCR methods. The amplification products were inserted into the cloning site of pcrSMART vector (Lucigen, Middleton, Wis.) and used to transform E. CLONI 10 G cells (Lucigen, Middleton, Wis.).

Example 4

Screening by Sequence Similarity 21,797 clones from the library described in Example 3 were sequenced using standard methods. These sequences were conceptually translated and compared to the database of non-redundant protein sequences in GenBank (NCBI) using the BLASTx program (NCBI). Of these, 9,092 had significant similarity to coding sequences of known proteins in the database. 2,036 had similarity to known viral coding sequences. 148 had at least partial similarity to known DNA polymerase coding sequences. 34 appear to be complete polymerase coding sequences.

Example 5

Expression of DNA Polymerase Genes 34 complete polymerase genes from the library described in Examples 3 and 4, as well as 24 additional viral genes from three other similarly prepared libraries, were constitutively expressed in the E. CLONI 10 G cells (Lucigen, Middleton, Wis.). The proteins were extracted, heated to 70° C. for 10 minutes and tested for DNA polymerase activity using a primer extension assay as follows.

A primer of 37 nucleotides having the sequence shown in SEQ ID NO:23, labeled on its 5' end with ROX, was annealed to a template of 41 nucleotides having the sequence shown in SEQ ID NO:24. Proteins extracted as described above and template were added to 20 mM Tris-HCl, 10 mM $(NH_4)_2SO_4$, 10 mM KCl, 2 mM $MgSO_4$, 0.1% Triton X-100, pH 8.8@25° C., and 250 µM each of deoxycytidine triphosphate (dCTP), deoxyadenine triphosphate (dATP), deoxyguanidine triphosphate (dGTP), and thymidine triphosphate (TTP). The reaction was incubated at 70° C. for 10 minutes. The reactions were analyzed using an ABI 310 Genetic Analyzer. Extension of the primer resulted in a mobility shift corresponding to an extension of 4 nucleotides that was detectable by the ABI 310 Genetic Analyzer. Of the 58 clones tested, a total of ten clones expressed detectable DNA polymerase (DNAP) activity. The clone number and corresponding polynucleotide sequence, polypeptide sequence, sequence similarity and E (expect)-values for these polymerases are shown below in Table 1. The presence of exonuclease activity, either 3'-5' or 5'-3', resulted in a reaction product migrating at less than 37 nucleotides during capillary electrophoresis.

TABLE 1

| Clone | Polynucleotide | Polypeptide | Strongest similarity | Expect value | % identity | % conserved | Exo |
|---|---|---|---|---|---|---|---|
| 3063 | SEQ ID NO. 1 | SEQ ID NO: 2 | *Aquifex pyrophilus* pol I | 0.0 | 63 | 79 | 3' |
| 488 | SEQ ID NO. 3 | SEQ ID NO: 4 | *Aquifex pyrophilus* pol I | $1 \times 10^{-46}$ | 33 | 51 | No |
| 3173 | SEQ ID NO. 5 | SEQ ID NO: 6 | *Desulfitobacterium hafniense* pol I | $2 \times 10^{-37}$ | 30 | 48 | 3' |
| 4110 | SEQ ID NO. 7 | SEQ ID NO: 8 | *Pyrodictium occultum* pol II | $3 \times 10^{-55}$ | 28 | 46 | No |
| 2323 | SEQ ID NO. 9 | SEQ ID NO: 10 | *Pyrobaculum aerophilum* pol II | $1 \times 10^{-47}$ | 28 | 45 | 3' |
| 653 | SEQ ID NO. 11 | SEQ ID NO: 12 | *Pyrococcus furiosus* virus pol | $2 \times 10^{-12}$ | 37 | 59 | 3' |
| 967 | SEQ ID NO. 13 | SEQ ID NO: 14 | *Aquifex aeolicus* pol I | $3 \times 10^{-44}$ | 36 | 53 | No |
| 2783 | SEQ ID NO. 15 | SEQ ID NO: 16 | *Sulfolobus tokodaii* pol II | $3 \times 10^{-56}$ | 27 | 46 | 3' |
| 2072 | SEQ ID NO. 17 | SEQ ID NO: 18 | *Sulfolobus tokodaii* pol II | $2 \times 10^{-10}$ | 39 | 60 | ND |
| 2123 | SEQ ID NO. 19 | SEQ ID NO: 20 | *Pyrococcus abyssi* pol II | $1 \times 10^{-4}$ | 35 | 51 | ND |

Example 6

Purification and Characterization of Viral DNA Polymerase Identified in the Viral Libraries As determined by sequence similarity screening described in Example 4, the polynucleotide having the sequence of nucleotides shown in SEQ ID NO:5 included regions having significant similarity to several dozen sequences encoding bacterial DNA polymerase I. The E value for the complete gene was as low as $2\times10^{-37}$, indicating a very high probability that the sequence is that of an authentic DNA polymerase gene. This coding sequence was transferred to a tac-promoter based expression vector (Lucigen) and used to produce high levels of thermostable DNA polymerase in E. CLONI 10 G cells according to the manufacturer's recommendations (Lucigen). The protein was purified by column chromatography.

To measure the activity of the polymerase, the purified protein was incubated with 50 μl of mix containing 0.25 mg/ml activated calf thymus DNA (Sigma), 200 μM each of deoxycytidine triphosphate (dCTP), deoxyadenine triphosphate (dATP), deoxyguanidine triphosphate (dGTP), and thymidine triphosphate (TTP), 100 μCi/ml of [α P-33] deoxycytidine triphosphate (Perkin-Elmer), 20 mM Tris-HCl, 10 mM $(NH_4)_2SO_4$, 10 mM KCl, 2 mM $MgSO_4$, 0.1% Triton X-100, pH 8.8@25° C. The reaction was incubated at 60° C. for 30 minutes. The reaction product (5 μl) was transferred to a DE81 filter (Whatman) and allowed to dry. The filter was washed with 3 changes of 5M sodium phosphate (pH 7.0), water and with ethanol. The filter was dried and incorporated label was measured in a scintillation counter. A blank reaction without added DNA polymerase was used to determine background activity. Activity of the polymerase was determined by the following equation, widely used in the art and reported in standard units:

Activity=(sample counts−blank)×(8 nmol dNTPs/reaction)×(1 unit/10 nmol dNTPs incorporated)

Counts of >1,000 cpm were detected compared to a typical background of <100 cpm, confirming the presence of DNA polymerase activity.

Example 7

Production of Exonuclease Deficient Polymerase 3173 Mutants

The presence of a 3'-5' exonuclease domain in the 3173 DNA polymerase was detected by reduction in molecular weight of a 5' fluorescently labeled oligonucleotide. Upon incubation of the primer/template complex described in Example 5, under the same conditions, a portion of the primer product was reduced in apparent molecular weight. This reduction in size was detected by capillary electrophoresis using an ABI 310 Genetic Analyzer operated in GeneScan mode. The presence of an exonuclease domain was confirmed by sequence alignment and by incubation of the polymerase with a radiolabeled polynucleotide, followed by digestion and precipitation with trichloroacetic acid. Radioactivity due to free nucleotides in the supernatant was measured.

Based on sequence alignments comparing polymerase 3173 with sequences identified in NCBI conserved domain database cdd.v2.07 (publicly available), an active site and apparent metal chelating amino acids (amino acids D49 and E51) were identified. Based on this information, two mutants of polymerase 3173 were produced. One mutant, D49A, was the result of a mutation of the aspartic acid at position 49 of the wild-type protein to alanine. The second mutant, E51A, was the result of a mutation of the glutamic acid at position 51 of the native protein to alanine. Mutants D49A and E51A were produced using standard methods.

An exonuclease assay was performed to confirm that exonuclease activity was eliminated in the mutants. Each of mutants D49A and E51A were tested for exonuclease activity using the radioactive nucleotide release assay described above, which is capable of detecting exonuclease activity levels below 0.1% of wild-type. Wild-type polymerase 3173 exhibited potent nuclease activity, whereas neither mutant exhibited detectable nuclease activity.

Example 8

Processivity of Polymerase 3173 Mutant D49A

Processivity was determined by annealing a fluorescently-labeled primer to a single-stranded M13 template (50 nM each). Polymerase 3173 mutant D49A was added (0.5 nM) and allowed to associate with the primed template. Nucleotides were added simultaneously with an "enzyme trap" comprised of an excess of activated calf thymus DNA (Sigma) (0.6 mg/ml final) and the reactions were incubated at 70° C. Samples were removed and the reactions were quenched by EDTA (10 mM) at 1, 3, 10, and 30 minutes. Extension of the primer before dissociation was measured by resolving the extension product on an ABI 310 Genetic Analyzer in GeneScan mode. Removal of product at the increasing time points resulted in increasingly high molecular weight product until a maximum was reached. The shortest time point giving maximal product size was used for the calculations. Peaks from the electropherograms were integrated by the GeneScan software and processivity was determined by the following equation:

Processivity=$[[(1\times I(1))]+[(2\times I(2))]+\ldots[(n)\times(I(n))]]/[I(1)+I(2)\ldots+I(n)]]$ where I=intensity of each peak, n=number of nt added.

The processivity for polymerase 3173 D49A was determined to be 47 nt.

Example 9

Characterization of Polymerase 3173

Exonuclease activity for polymerase 3173 was determined as described in Example 7.

The binding constant (reported as Km, the concentration at which the reaction rate is 50% maximal) for nucleotides by polymerase 3173 was determined using activated calf thymus DNA as a template. Reactions were maintained under pseudo-first order conditions using a molar excess of all components, with the exceptions of the enzyme and the nucleotides. Reactions (50 μl) were incubated at 70° C. and samples (5 μl each) were removed at varying time points and spotted on DE81 paper. Activity was determined as described in Example 6. The binding constant for primed template was similarly determined except that nucleotides were supplied in excess and the concentration of primed template (primed single stranded M13 DNA) was varied. Results are tabulated below.

| Activity | 3173 |
| --- | --- |
| 5'-3' exonuclease activity | — |
| 3'-5' exonuclease activity | strong |
| Strand displacement | strong |
| Extension from nicks | strong |
| Thermostability (T$_{1/2}$ at 95°) | 10 min. |
| Km dNTPs | 20-40 µM |
| Km DNA | 5.3 nM |
| Fidelity | 6.98 × 10$^4$ |

Figure 5:
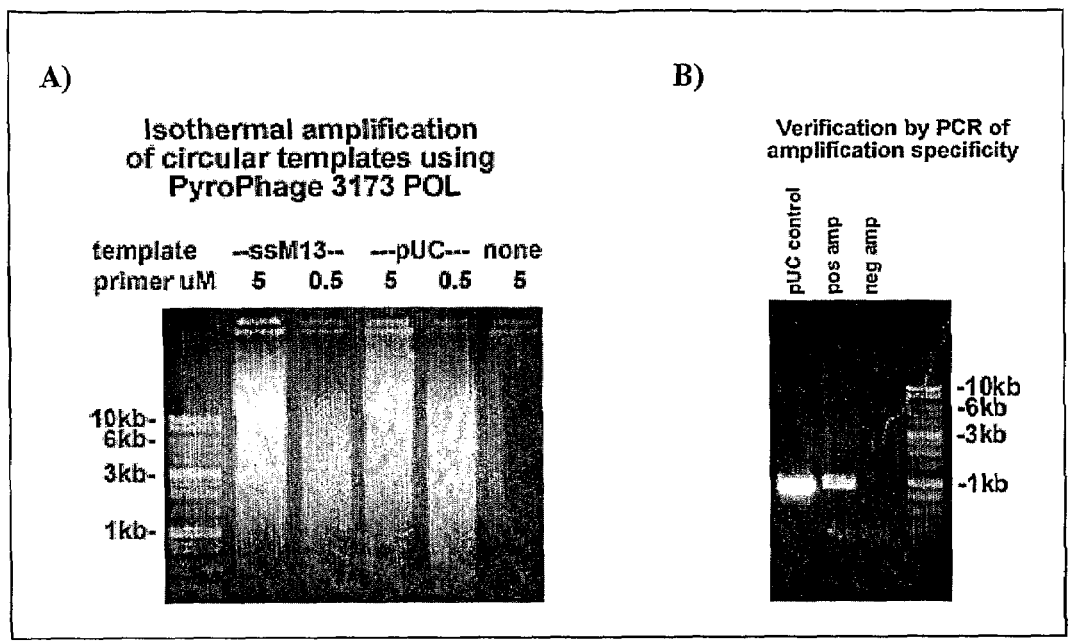
FIG. 5 shows photographic images of two electrophoretic gels, one used to resolve an isothermal amplification reaction (panel A) in which single-stranded and double-stranded templates were amplified using a polymerase of the invention and a PCR amplification reaction (panel B) used to verify the identity of the isothermal amplification product.
Figure 6:
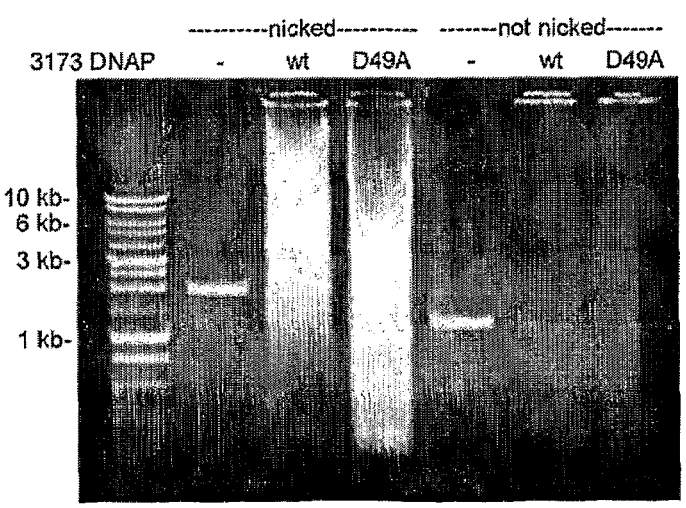
FIG. 6 is a photographic image of an electrophoretic gel used to resolve amplification reactions carried out without added primers using two polymerases of the invention in the presence or absence of a commercially available nicking enzyme.

Strand displacement activity was determined using primer-initiated synthesis in a rolling circle amplification (RCA) protocol. Briefly, polymerase 3173 was incubated in the presence of a plasmid and random primers. Polymerase 3173 extended the primer the complete circumference of the plasmid at which point the 5' end of the primer was encountered. Polymerase 3173 displaced the nascent strand of DNA and continued DNA synthesis. The presence of strand displacement activity resulted in a product having a molecular weight greater than the original template. As shown in FIGS. 5 and 6, the higher molecular weight product was easily detected by agarose gel electrophoresis.

Fidelity was determined as described in example 10.

Example 10

High Fidelity PCR Using Polymerase 3173

Fidelity was determined by a modification of the standard assay in which the lacIq gene is amplified by the DNA polymerase of interest and inserted into a plasmid containing genes encoding a functional lacZ alpha peptide and a selectable marker. Primers of SEQ ID NOS:28 and 29 were used to amplify a sequence containing both the lacIq and the KanR gene. Insertion of this gene into the Eco109I site of pUC19 resulted in double resistance to kanamycin and ampicillin. Normally a white phenotype is seen for clone containing this construct when plated on X-Gal. Mutation of the lacIq results in a blue phenotype for the colonies when plated on X-Gal. The wild-type (proofreading) DNA polymerase 3173 and its exonuclease deficient derivatives, E51A and D49A, and, for comparison, two standard DNA polymerases, Taq and VENT$_R$ DNA polymerases, were tested.

For high fidelity PCR amplification, five units of the wild-type (proofreading) DNA polymerase 3173 (SEQ ID NO: 6) was tested using the following mix (50 mM Tris HCl (pH 9.0 at 25° C.), 50 mM KCl, 10 mM (NH$_4$)$_2$SO$_4$, 1.5 mM MgSO$_4$, 1.5 mM MgCl$_2$, 0.1% triton-X100, 250 mM ectoine and 0.2 mM each of dGTP, dATP, dTTP and dCTP. Opposing primers of SEQ ID 28 and 29 (1 µM each) amplified the expected 2 k kb product from template SEQ ID 30 (10 ng). After thermal cycling (94° C. for 1 minute, 25 cycles of (94° C. for 15 seconds, 60° C. for 15 seconds, 72° C. for 2.5 minutes) and 72° C. 7 minutes), reaction products were quantified to determine "fold amplification," (see below) using agarose gel electrophoresis. Both primers contain Eco109I sites. The PCR product was digested with Eco109I and inserted into the Eco109I site of pUC19. 10 G cells transformed by the construct were plated on LB plates containing ampicillin (100 µg/ml), kanamycin (30 µg/ml) and X-Gal (50 µg/ml). Blue and white colony counts were used for the fidelity determinations. For comparison, polymerase 3173 exonuclease deficient mutants, E51A and D49A and, two standard DNA polymerases, Taq and VENT$_R$ DNA polymerases, were tested in the same manner.

As is standard in the art, fidelity was determined based on the ratio of blue:white colonies using the following equation:

$$\text{fidelity} = -\ln F/d \times t$$

where F=fraction of white colonies, d=number of duplications during PCR (log2 of fold amplification) and t is the effective target size (349 for lacIq). The results of the fidelity assay are tabulated below

| DNA polymerase | fidelity |
| --- | --- |
| DNA polymerase 3173 | 6.98E+04 |
| DNA polymerase 3173 (E51A) | 1.28E+04 |
| DNA polymerase 3173 (D49A) | 1.88E+04 |
| Taq | 9.76E+03 |
| VENT$_R$ | 2.42E+04 |

Example 11

Polymerase Chain Reaction Using Polymerase 3173 Mutant D49A

Primers specific for the bla gene of pUC19 were used to amplify a 1 kb product using polymerase 3173 mutant D49A and commercial enzymes for comparison. The polymerase chain reactions included 50 mM Tris HCl (pH 9.0 at 25° C.), 50 mM KCl, 10 mM (NH$_4$)$_2$SO$_4$, 1.5 mM MgSO$_4$, 1.5 mM MgCl$_2$, 0.1% triton-X100, 0.02 mg/ml bovine serum albumin, 250 mM ectoine and 0.2 mM each of dGTP, dATP, dTTP and dCTP. Opposing primers annealing 1 kb apart in the bla gene of the pUC19 plasmid and the D49A mutant polymerase were added. After thermal cycling (25 cycles of 94° C. for 15 seconds, 60° C. for 15 seconds, 72° C. for 60 seconds), reactions were resolved using agarose gel electrophoresis.

The results are shown in FIG. 1. Lanes are as follows: no template DNA (lane 2) or 40 nanograms of pUC19 DNA (lanes 3-8); no enzyme (lanes 2 and 3), 2, 4 or 8 Units of polymerase 3173 mutant D49A (P, lanes 4, 5 and 6, respectively), 5 U VENT$_R$ (V, NEB, lane 7) or 5 U Taq DNA polymerase (T, Lucigen, lane 8). Also shown are molecular weight markers (lane 1).

As seen in FIG. 1, PCR amplification using the D49A mutant resulted in a product of the predicted size, similar to commercially available enzymes.

Example 12

Figure 2:
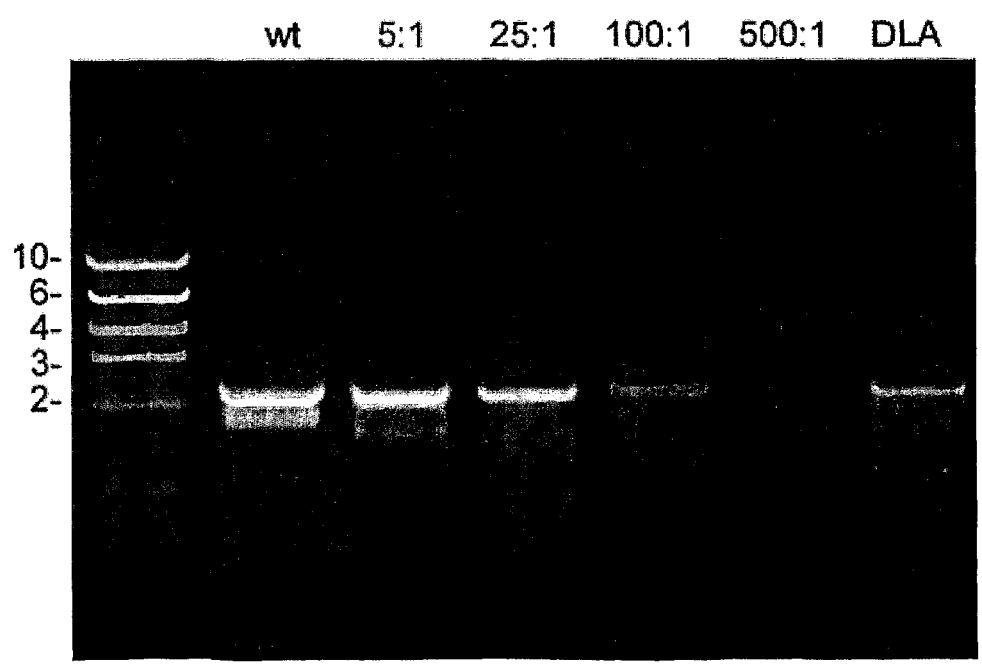
FIG. 2 is a photographic image of an electrophoretic gel showing the results of PCR amplification using a polymerase of the invention.

Polymerase Chain Reaction Using Polymerase 3173 and Polymerase 3173 Mutant E51A A range of mixes of polymerase 3173 and polymerase 3173 mutant E51A (1:5, 1:25, 1:100, 1:500 U/U), and primers of SEQ ID NO:28 and SEQ ID NO:29, were used to amplify a 2259 nucleotide region of a circular synthetic template. The amplification mix, comprised of 50 mM Tris HCl (pH 9.0 at 25° C.), 50 mM KCl, 10 mM (NH$_4$)$_2$SO$_4$, 1.5 mM MgSO$_4$, 1.5 mM MgCl$_2$, 0.1% triton-X100, 15% sucrose, 0.2 mM each of dGTP, dATP, dTTP and dCTP, 1 µM of each opposing primer and 20 ng of template, was incubated under the following conditions: 94° C. for 2 minutes, 25 cycles of (94° C. for 15 seconds, 69° C. for 15 seconds, 72° C. for 2 minutes) and 72° C. for 10 minutes. The amplification reaction resulted in product migrating at the expected molecular weight with no extraneous products as seen in FIG. 2.

Example 13

PCR Amplification of the cyc Gene from *Bacillus stearothermophilus*

The cyc gene from a *Bacillus stearothermophilus* isolate had proven to be an amplification-resistant sequence by all commercially available DNA polymerases that were tested. This sequence was amplified using polymerase 3173 mutant D49A using the conditions described in Example 10. For comparison, amplification of this gene by other commercially available DNA polymerases including Taq, Phusion (Finnzymes), VENT$_R$, Tfl (Promega), KOD (TaKaRa) was also conducted according to each manufacturers' recommendations.

Figure 3:
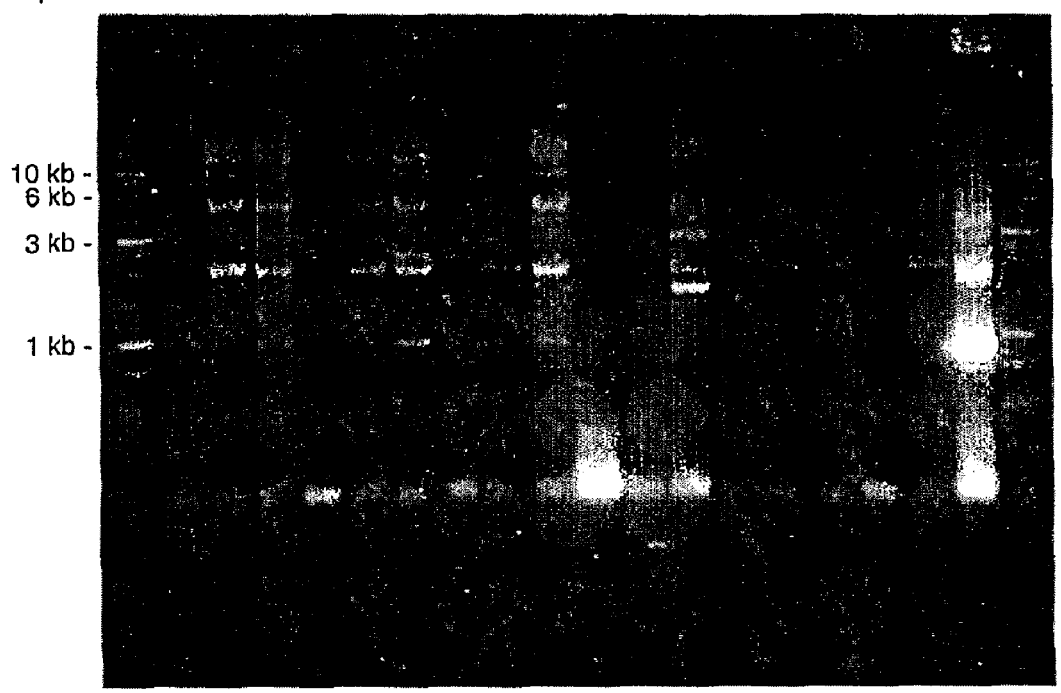
FIG. 3 is a photographic image of an electrophoretic gel showing results of PCR amplification of a 1 kb *Bacillus* cyc gene sequence (a guanidine/cytosine-rich template) using a polymerase of the invention and five commercially available polymerases.

The results are shown in FIG. 3. Lanes are as follows: Taq (lanes 2-4), Phusion (lanes 5-7), VENT$_R$ (lanes 8-10), Tfl (lanes 11-13), KOD (lanes 14-16) and polymerase 3173 mutant D49A (lanes 17-19). Amplification products were resolved by agarose gel electrophoresis and imaged using standard methods. The predicted amplification product comigrates with the 1 kb marker (lanes 1 and 20). Negative control reaction lacking template (lanes 2, 5, 8, 11, 14 and 17) or enzyme (lanes 3, 6, 9, 12, 15 and 18) are also shown in FIG. 3.

As shown in FIG. 3, amplification was observed using commercially available enzymes, as well as the D49A mutant, however, none of these commercially available enzymes resulted in the exceptionally high yields generated using mutant D49A.

Example 14

Reverse Transcriptase Activity and RT-PCR Using Polymerase 3173 and Polymerase 3173 Mutants Reverse transcriptase activity was detected by incorporation of radiolabeled deoxyribonucleotide triphosphates into polydeoxyribonucleotides using a ribonucleic acid template. A reaction mix comprising 50 mM Tris-HCl pH 8.3 at 25° C., 75 mM KCl, 3 mM MgCl$_2$, 2 mM MnCl$_2$, 200 µM dTTP, 0.02 mg/ml Poly rA: Oligo dT (Amersham), and 10 µCi of [P-32] alpha dTTP was incubated with 1 U of polymerase 3173 or the polymerase 3173 mutant D49A at 60° C. for 20 minutes. Incorporation of dTTP was detected as radioactive counts adhering to DE81 filter paper. Similar reverse transcription reactions were measured by incorporation of labeled dTTP on a poly rA template using 1 unit of Tth (Promega) and 1 unit MMLV reverse transcriptase (Novagen) according to the respective manufacturers' recommended conditions. Incorporation rates of polymerase 3173 and mutant D49A in comparison to commercially available enzymes are tabulated below.

| Enzyme | Incorporation of dTTP |
|---|---|
| 3173 wt | 1.037 nmoles |
| 3173 (D49A) | 1.507 nmoles |
| Tth DNA polymerase | 0.802 nmoles |
| MMLV reverse transcriptase | 1.110 nmoles |

In addition, in contrast to the manganese-dependent activity of Tth, reverse transcription by polymerase 3173 and mutant D49A is equivalent when reactions are run in the presence of either manganese or magnesium.

Figure 4:
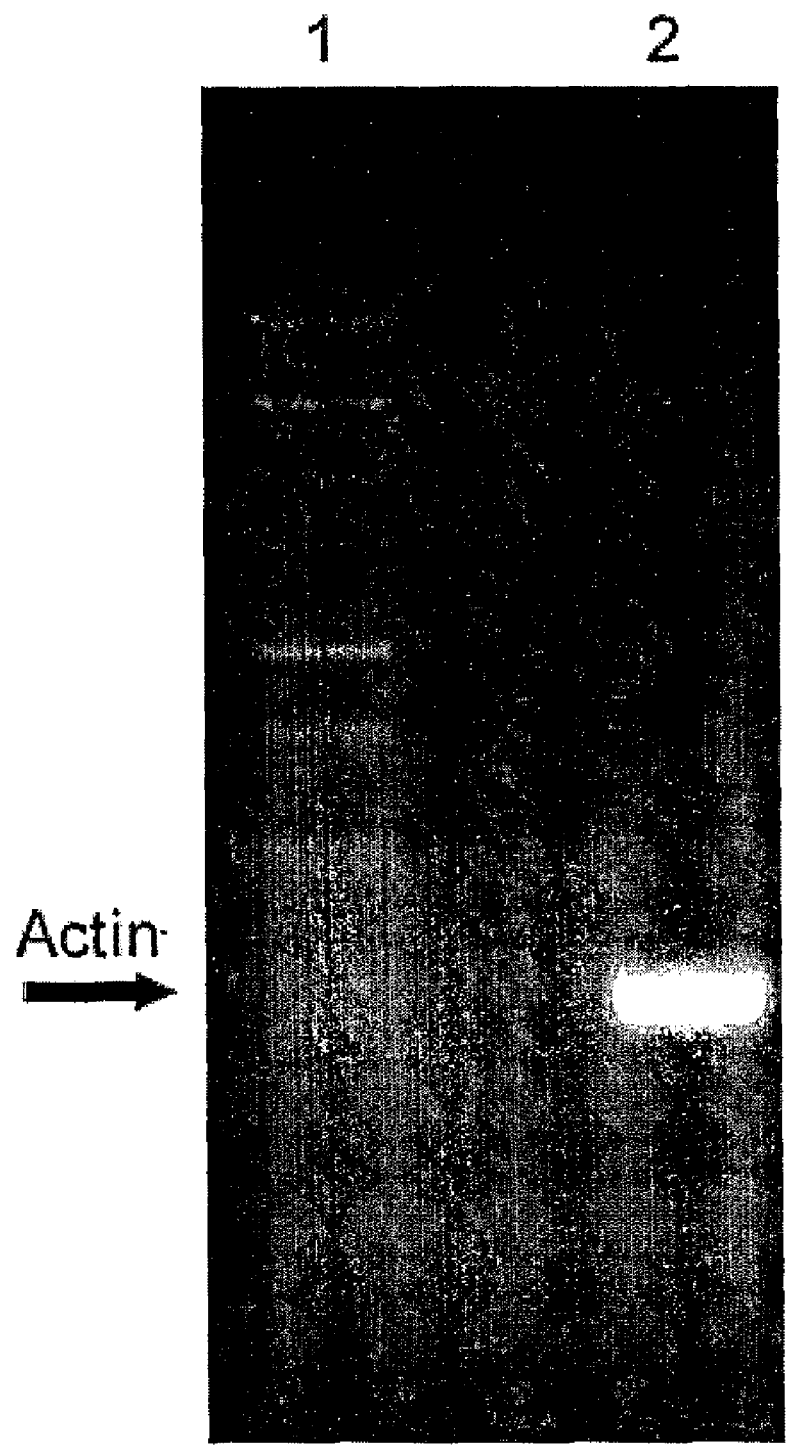
FIG. 4 is a photographic image of an electrophoretic gel used to resolve the product of an RT-PCR reaction in which a 294 bp cDNA was reverse-transcribed and amplified from total mouse RNA using specific primers and a polymerase of the invention.

Next, a 50 µl reaction containing 20 mM Tris-HCl (pH 8.8 at 25° C.), 10 mM (NH4)2SO4, 10 mM KCl, 2 mM MgSO4, 0.1% Triton X-100, 0.25M ectoine, 200 µM each of dGTP, dATP, dTTP and dCTP, 1 µg of total mouse liver RNA (Ambion), 0.4 µM of primers from the QuantumRNA β-actin Internal Standards kit (Ambion) and 5 units of polymerase 3173 mutant E51A DNA polymerase was incubated under the following temperature cycle: 60° for 60 minute, 94° C. for 2 minutes, 35 cycles of (94° C. for 15 seconds, 57° C. for 15 seconds, 72° C. for 1 minute), followed by 72° C. for 10 minutes. The primers are predicted to direct synthesis of a 294 base-pair product. Five µl of the reaction was analyzed by agarose gel electrophoresis. As shown in FIG. 4, a prominent band was observed migrating at the predicted molecular weight; no other bands were observed.

Example 15

High Temperature Isothermal RCA Amplification

Five units of polymerase 3173 was used to amplify one nanogram each of single-stranded M13mp18 and double stranded pUC19 plasmid DNA. Reactions contained 20 mM Tris-HCl, 10 mM (NH$_4$)$_2$SO$_4$, 10 mM KCl, 2 mM MgSO$_4$, 0.1% Triton X-100, pH 8.8 at 25° C., and 250 µM each of dGTP, dATP, dTTP and dCTP. Either 0.5 µM or 5 µM of random decamer primers were added to each template. Reactions were incubated at 95° C. prior to addition of enzyme, then 16 hours at 55° C. with enzyme. One fiftieth of each reaction was resolved on a 1% agarose gel.

Results are shown in FIG. 5, Panel A. Lanes are as follows: five units of 3173 wild type DNA polymerase used to amplify M13mp18 single-stranded DNA template (lanes 2 and 3) and pUC19 double-stranded DNA (lanes 4 and 5) or no template (lane 6). Random ten nucleotide oligomer primers are added in the concentrations of 5 µM (lanes 2, 4 and 6) or 0.5 µM (lanes 3 and 5).

As shown in FIG. 5, panel A, polymerase 3173 amplified both single- and double-stranded DNA templates. The estimated overall yield was approximately 50 µg for both templates, indicating amplification of up to 50,000-fold. A negative control reaction lacking template resulted in no significant yield of amplification product.

To determine if the amplification was specific for the template DNA, one µl of the amplification product of the positive pUC19 reaction was tested in a PCR reaction using primers specific for a 1 kb sequence in the bla gene of the original plasmid template. As a negative control, a reaction lacking deoxynucleotides was analyzed using PCR. As a positive control, the 1 kb sequence was amplified directly from 1 ng of pUC19.

Results are shown in FIG. 5, Panel B. Lane 1 shows positive control amplification of the 1 kb bla gene sequence of pUC19. Lane 2 shows amplification of the bla gene from the product amplified as described above. Lane 3 shows the results for the negative control.

As expected, authentic amplification product was obtained using polymerase 3173. The 1 kb amplification product was detected by PCR in the test amplification reaction and in the positive control reaction, but not in the negative control amplification reaction.

Example 16

Isothermal RCA in the Absence of Added Primers

Reactions containing 10 ng of plasmid DNA, 20 mM Tris-HCl, 10 mM (NH$_4$)$_2$SO$_4$, 10 mM KCl, 2 mM MgSO$_4$, 0.1%

Triton X-100, pH 8.8 at 25° C., and 200 μM each of dGTP, dATP, dTTP and dCTP were incubated for 2 hours at 56° C. with or without 10 units of nick-generating enzyme N.Bst NB1 (NEB) and either no DNA polymerase, 200 units of 3173 wt or 400 units of 3173 (D49A) mutant enzyme. Parallel reactions were performed in the absence of nicking enzyme, polymerase or both. Amplification products were analyzed by agarose gel electrophoresis.

Results are shown in FIG. 6. Lanes are as follows: Nicking enzyme present (lanes 2-4) or absent (lanes 5-7). Polymerase 3173 (lanes 3 and 6) or D49A mutant (lanes 4 and 7).

As shown in FIG. 6, multi-microgram yields of DNA product were obtained in the presence of both polymerase 3173 and the polymerase 3173 mutant D49A when the nicking enzyme was present, but not the absence of DNA polymerase or nicking enzyme.

Example 17

Mutagenesis of the Polymerase Domain to Reduce Nucleotide Discrimination

A 5' Rox-labeled primer complementary to M13mp18 nucleotides 6532 to 6571 (5 nM) was annealed to single-stranded M13mp18 DNA (10 nM) in a buffer containing 20 mM Tris-HCl, 10 mM $(NH_4)_2SO_4$, 10 mM KCl, 2 mM $MgSO_4$, 0.1% Triton X-100, pH 8.8 at 25° C., and 50 μM each of dGTP, dATP, dTTP and dCTP. In separate reactions, ddGTP, ddATP, ddTTP, and ddCTP were added to the above mix in concentrations of 50, 500 and 5000 μM each. Five units of polymerase 3173 mutant D49A were added and the reactions were incubated for 30 minutes at 70° C. Extension of the primer was detected by the ABI 310 Genetic Analyzer in Gene Scan mode. In this experiment, no inhibition of primer extension was detected, even at a 100-fold molar excess of chain terminator, suggesting a strong discrimination against the analogs by polymerase 3173 mutant D49A.

In a second experiment, incorporation was tested by detection of DNA synthesis using a double-strand specific fluorescent dye, Pico Green (Invitrogen). Unlabeled M13 primer (2 μM) was added to M13mp18 ssDNA (1.2 μM) in buffer containing 20 mM Tris-HCl, 10 mM $(NH_4)_2SO_4$, 10 mM KCl, 2 mM $MgSO_4$, 0.1% Triton X-100, pH 8.8 at 25° C., and 2 mM each of dGTP, dATP, dTTP and dCTP. In separate reactions, a mix of ddGTP, ddATP ddTTP, ddCTP (2 mM each) and a mix of the four acyNTPs (2 mM each) were added to extension reactions followed by DNA polymerase. As a control, identical reactions without added chain terminating analogs were also performed. Polymerase 3173 mutant D49A was tested and, for comparison, T7 DNA polymerase, which incorporates ddNTPs with very low discrimination, and Klenow fragment of E. coli polymerase I and $VENT_R$ DNA polymerase (New England Biolabs), both of which have a higher discrimination, were also tested. Extension of the primer was detected by fluorescence of Pico Green dye.

The results are tabulated below. Inhibition of the polymerase 3173 mutant D49A enzyme by chain terminators was minimal.

|  | 3173 D49A | T7 | Klenow | $VENT_R$ |
| --- | --- | --- | --- | --- |
| dNTPs | 100.0% | 100.0% | 100.0% | 100.0% |
| ddNTPs | 66.0% | 17.7% | 49.4% | 85.5% |
| acycloNTPs | 84.0% | 32.3% | 73.8% | 67.3% |

Based on alignment with family A DNA polymerases, amino acid 418 of the polymerase 3173 mutant D49A was mutated from phenylalanine to tyrosine. The mutant protein was expressed and the cells lysed and heat-treated at 70° C. for 10 minutes to inactivate host proteins. The polymerase 3173 mutant D49A/F418Y was tested for inhibition of radioactive nucleotide incorporation using chain terminating nucleotide analogs in the same mix as unlabeled deoxynucleotides. A reaction including 20 mM Tris-HCl, 10 mM $(NH_4)_2SO_4$, 10 mM KCl, 2 mM $MgSO_4$, 0.1% Triton X-100, pH 8.8 at 25° C., 0.25 mg/ml activated ct DNA, 40 μM each of dGTP, dATP, dTTP and dCTP and 0.1 μCi [α P-33] dCTP was used. In separate reactions both the D49A/F418Y mutant and purified polymerase 3173 mutant D49A were tested for inhibition by 4 mM each of ddNTPs and 4 mM each acycloNTPs. A control with no chain terminators was included. 50 μl reactions were incubated at 70° C. for 30 min. 15 μl of each reaction was spotted on DE81 paper, washed and counted, and units of activity were determined as described in Example 6. The degree of inhibition due to incorporation of dideoxy- and acyclo-nucleotides is tabulated below.

|  | no terminators | ddNTPs | acyNTPs |
| --- | --- | --- | --- |
| 3173 D49A | 100.0% | 92.6% | 97.7% |
| 3173 D49A/F418Y | 100.0% | 0.8% | 1.1% |

The polymerase 3173 double mutant D49A/F418Y was also tested in the fluorescent primer extension assay described above. A 2× ratio of ddGTP:dGTP almost completely inhibited any extension. A 0.2× ratio of ddGTP:dGTP resulted in nearly complete inhibition of primer extension, with no extension continuing beyond the fourth G residue. Together, this data suggests that discrimination by the polymerase 3173 mutant D49A/F418Y against the chain terminating nucleotides that were tested is nearly zero.

The invention has been described with reference to various specific embodiments and techniques. However, it should be understood that many variations and modifications may be made while remaining within the spirit and scope of the invention.

We claim:

1. A substantially purified polymerase having an amino acid sequence comprising SEQ ID NO:6, sequence variants at least about 95% identical to SEQ ID NO:6, or fragments of SEQ ID NO:6 retaining polymerase activity.

2. The polymerase of claim 1, wherein the polymerase:
   comprises aspartate at a position corresponding to position 49 of SEQ ID NO:6 and glutamate at a position corresponding to position 51 of SEQ ID NO:6; and
   exhibits exonuclease activity.

3. The polymerase of claim 2 having an amino acid sequence comprising SEQ ID NO:6.

4. The polymerase of claim 1, wherein the polymerase:
   comprises a residue other than aspartate at a position corresponding to position 49 of SEQ ID NO:6, a residue other than a glutamate at a position corresponding to position 51 of SEQ ID NO:6, or a residue other than aspartate at a position corresponding to position 49 of SEQ ID NO:6 and a residue other than a glutamate at a position corresponding to position 51 of SEQ ID NO:6; and
   substantially lacks exonuclease activity.

5. The polymerase of claim 4 having an amino acid sequence comprising SEQ ID NO:25, SEQ ID NO:26, or SEQ ID NO:27.

6. The polymerase of claim 1, wherein the polymerase:
   comprises tyrosine at a position corresponding to position 418 of SEQ ID NO:6; and
   has a relative incorporation efficiency of nucleotide analogs that is at least 10% of the incorporation efficiency of standard deoxynucleotides.

7. The polymerase of claim 6 having an amino acid sequence comprising SEQ ID NO:26 or SEQ ID NO:27.

8. The polymerase of claim 1, wherein the polymerase;
   comprises a residue other than aspartate at a position corresponding to position 49 of SEQ ID NO:6, a residue other than a glutamate at a position corresponding to position 51 of SEQ ID NO:6, or a residue other than aspartate at a position corresponding to position 49 of SEQ ID NO:6 and a residue other than a glutamate at a position corresponding to position 51 of SEQ ID NO:6;
   comprises tyrosine at a position corresponding to position 418 of SEQ ID NO:6; and
   substantially lacks exonuclease activity and has a relative incorporation efficiency of nucleotide analogs that is at least 10% of the incorporation efficiency of standard deoxynucleotides.

9. The polymerase of claim 8 having an amino acid sequence comprising SEQ ID NO:26 or SEQ ID NO:27.

10. The polymerase of claim 1 wherein the polymerase exhibits reverse transcriptase activity.

11. The polymerase of claim 10 having an amino acid sequence comprising SEQ ID NO:6, SEQ ID NO.25, SEQ ID NO:26, or SEQ ID NO: NO:27.

12. The polymerase of claim 1 wherein the polymerase exhibits strand displacement activity.

13. The polymerase of claim 12 having an amino acid sequence comprising SEQ ID NO:6, SEQ ID NO:25, SEQ ID NO:26, or SEQ ID NO: NO:27.

14. The polymerase of claim 1 having the amino acid sequence comprising SEQ ID NO: 6 or sequence variants at least about 95% identical thereto.

15. The polymerase of claim 14 comprising at least one amino acid substitution or deletion in the sequence of amino acids from residue 30 to residue 190 of SEQ ID NO:6, wherein the polypeptide substantially lacks exonuclease activity.

16. The polymerase of claim 15 comprising a substitution of a residue corresponding to position 49 or position 51 of SEQ ID NO:6.

17. The polymerase of claim 16 comprising the sequence of SEQ ID NO:25.

18. The polymerase of claim 16 comprising the sequence of SEQ ID NO:26.

19. The polymerase of claim 16 further comprising a substitution of a residue corresponding to position 418 of SEQ ID NO:6.

20. The polymerase of claim 19 comprising the sequence of SEQ ID NO:26 or SEQ ID NO: NO:27.

21. A composition comprising one or more polymerases from the group consisting of SEQ ID NO:6, sequence variants at least about 95% identical to SEQ ID NO:6, and fragments of SEO ID NO:6 retaining polymerase activity.

22. The composition of claim 21 comprising a polymerase having SEQ ID NO:6 or a sequence variant at least about 95% identical thereto and one or more polymerases selected from the group consisting of SEQ ID NO:25, SEQ ID NO:26, SEQ ID NO:27 and a sequence variant at least about 95% identical thereto.

23. A method of producing the polymerase of claim 1 comprising expressing an isolated polynucleotide encoding the polymerase of claim 1.

24. The method of claim 23, wherein the isolated polynucleotide encodes an amino acid sequence comprising SEQ ID NO: 6 or sequence variants at least about 95% identical thereto.

25. The method of claim 24, wherein the isolated polynucleotide comprises the sequence of SEQ ID NO: 5.

26. The method of claim 23, wherein the isolated polynucleotide is included in a construct operably connected to a promoter.

27. The method of claim 26 wherein the construct is included in a recombinant host cell.

28. A method of synthesizing a copy or complement of a polynucleotide template comprising contacting the template with the polymerase of claim 1 under conditions sufficient to promote synthesis of the copy or complement.

29. The method of claim 28, wherein the template is RNA.

30. The method of claim 28, wherein the template is DNA.

31. The method of claim 28, wherein the conditions comprise maintaining substantially isothermal conditions.

32. The method of claim 28, wherein the conditions comprise thermocycling.

33. The method of claim 28, wherein the conditions comprise the presence of at least one primer pair.

34. The method of claim 28, wherein the conditions exclude manganese.

35. The method of claim 28, wherein the polynucleotide template comprises an amplification-resistant sequence.

36. The method of claim 35, wherein the amplification-resistant sequence comprises direct repeats, inverted repeats, at least 65% G +C residues or A +T residues or a sequence of greater than about 2 kilobases.

37. The method of claim 28, wherein the conditions comprise the presence of a nick-inducing agent.

38. The method of claim 37, wherein the conditions exclude primers.

39. A method of incorporating a nucleotide analog in a polynucleotide comprising contacting a template of the polynucleotide with the polymerase of claim 6 in the presence of the nucleotide analog.

40. The method of claim 39, wherein the nucleotide analog is a chain-terminating analog.

41. The method of claim 39, wherein the nucleotide analog is an acyclonucleotide or a dideoxynucleotide.

42. A method of sequencing a polynucleotide comprising a step of contacting the polynucleotide with the polymerase of claim 6 in the presence of a chain-terminating nucleotide analog.

43. The polymerase of claim 1 comprising a motif consisting of KSANFGLIYG (residues 414-423 of SEQ ID NO:6) or KSANYGLIYG (residues 414-423 of SEQ ID NO:26).

* * * * *

SEQUENCE LISTING

<160> NUMBER OF SEQ ID NOS: 29

<210> SEQ ID NO 1
<211> LENGTH: 1743
<212> TYPE: DNA
<213> ORGANISM: Unknown
<220> FEATURE:

<223> OTHER INFORMATION: Uncultured newly isolated virus

<400> SEQUENCE: 1

```
atgaaggtga gctttgaata catcacatct ccaaaatccc ttgccaagtg ggaagggagc      60
tttaaggata tacccttttt gtatattgat acgaaacgg tgggagacag caccataagg     120
ctcgtccaat tgggaactga aaaagacata ctcctttgg acctattcga gcttggtgat     180
gtaggaatta actttttaaa ggaactgctt tcccagaagg gtatagtggg tcataatcta     240
aagtttgacc tgaagtatct acttggctat ggaatagagc cctacgcagt ctttgacacc     300
atgatcgcca gtcagctgtt gggggactcc gacaggcact cccttcagaa attagccatg     360
cagtatttgg gagaggtcat agacaagagc cttcagcttt ccaactgggg ctcctcaagg     420
ctctcaaagg aacagttaga atatgccgcc ctggatgtgg atgtagtcag aaggctcttt     480
ccactgctcc ttgagaggtt aaacagtctt acaccgatgg tggaggaaaa ccttcttaaa     540
accaggaccg caaggtcttt gggctaaaa accccatcg ccatagtgga aatggctttt      600
gttcaggagg tggcaaagct tgaaagaaac gggctcccgg tggatgtgga agaactggaa     660
aggcttgtaa aggagcttc aaaggagctt caaaaaaggg tgatggactt tttagtcaaa      720
tacagaacgg accccatgtc tcccaaacag gtgggagagc ttttggtcaa aaagtttggc     780
ttgaaccttc caaaaacaga aaagggcaac atatccaccg atgacaaata cttggcggaa     840
cacatagaaa accctgcggt aagagaactt ttgaagataa gagagataaa aaagaacttg     900
gacaagcttg aggagattaa ggatggtttg agggggaaaa gggtatatcc agagttcaag     960
cagataggtg caataaccgg gcgaatgtcc tccatgaacc ccaacgtgca gaacattcca    1020
agggcctaa aagaatctt taaggcggag aaggaaatg ttttgtgat agcggacttt       1080
tctcaaatag agctgagaat cgccgcagag tacgtaaacg atgagagtat gataaaggta    1140
tttaggggaag ggagggatat gcacaaatac actgccagcg tgctcttggg gaaaaaggag   1200
gaagaaatta caaaggaaga gaggcagttg gcaaaggcgg taaattttgg gctcatatac    1260
ggcatatccg caagggttt ggcagaatac gcttactctt cctacggcat agccccttcc     1320
cttgcagaag cggagaaaat aagggcaaga ttttttgaac acttcagagg ctttaaggat    1380
tggcacgaaa gagttaagaa agaattaagg gaaaaggta atcagaggg ttatacctt       1440
cttggcagaa gatacacccg ccacaccttc ccagacgcgg tcaattatcc catcagggga    1500
actggtgcgg acctcttaaa actctctgtg ctcatatttg acgcagaggt cagaagggaa    1560
aacatcaaag cccgtgtgat aaacttggtg catgacgaga tagtggtgga atgtcccatg    1620
gaggagggag aaaggactgc ggagcttttg gagagggcta tgaaaagggc tggtgggatt    1680
atactaaaga aggtgcctgt ggaagtagag tgtgtgataa aggagaggtg ggaaaaggaa    1740
taa                                                                 1743
```

<210> SEQ ID NO 2
<211> LENGTH: 580
<212> TYPE: PRT
<213> ORGANISM: Unknown
<220> FEATURE:
<223> OTHER INFORMATION: Uncultured newly isolated virus

<400> SEQUENCE: 2

Met Lys Val Ser Phe Glu Tyr Ile Thr Ser Pro Lys Ser Leu Ala Lys
1               5                   10                  15

Trp Glu Gly Ser Phe Lys Asp Ile Pro Phe Leu Tyr Ile Asp Thr Glu
            20                  25                  30

```
Thr Val Gly Asp Ser Thr Ile Arg Leu Val Gln Leu Gly Thr Glu Lys
         35                  40                  45

Asp Ile Leu Leu Leu Asp Leu Phe Glu Leu Gly Asp Val Gly Ile Asn
 50                  55                  60

Phe Leu Lys Glu Leu Leu Ser Gln Lys Gly Ile Val Gly His Asn Leu
 65                  70                  75                  80

Lys Phe Asp Leu Lys Tyr Leu Leu Gly Tyr Gly Ile Glu Pro Tyr Ala
                 85                  90                  95

Val Phe Asp Thr Met Ile Ala Ser Gln Leu Leu Gly Asp Ser Asp Arg
             100                 105                 110

His Ser Leu Gln Lys Leu Ala Met Gln Tyr Leu Gly Glu Val Ile Asp
             115                 120                 125

Lys Ser Leu Gln Leu Ser Asn Trp Gly Ser Ser Arg Leu Ser Lys Glu
130                 135                 140

Gln Leu Glu Tyr Ala Ala Leu Asp Val Asp Val Val Arg Arg Leu Phe
145                 150                 155                 160

Pro Leu Leu Leu Glu Arg Leu Asn Ser Leu Thr Pro Met Val Glu Glu
                 165                 170                 175

Asn Leu Leu Lys Thr Arg Thr Ala Lys Val Phe Gly Leu Lys Asn Pro
             180                 185                 190

Ile Ala Ile Val Glu Met Ala Phe Val Gln Glu Val Ala Lys Leu Glu
             195                 200                 205

Arg Asn Gly Leu Pro Val Asp Val Glu Glu Leu Glu Arg Leu Val Lys
             210                 215                 220

Glu Leu Ser Lys Glu Leu Gln Lys Arg Val Met Asp Phe Leu Val Lys
225                 230                 235                 240

Tyr Arg Thr Asp Pro Met Ser Pro Lys Gln Val Gly Glu Leu Leu Val
                 245                 250                 255

Lys Lys Phe Gly Leu Asn Leu Pro Lys Thr Glu Lys Gly Asn Ile Ser
                 260                 265                 270

Thr Asp Asp Lys Tyr Leu Ala Glu His Ile Glu Asn Pro Ala Val Arg
             275                 280                 285

Glu Leu Leu Lys Ile Arg Glu Ile Lys Lys Asn Leu Asp Lys Leu Glu
             290                 295                 300

Glu Ile Lys Asp Gly Leu Arg Gly Lys Arg Val Tyr Pro Glu Phe Lys
305                 310                 315                 320

Gln Ile Gly Ala Ile Thr Gly Arg Met Ser Ser Met Asn Pro Asn Val
                 325                 330                 335

Gln Asn Ile Pro Arg Gly Leu Arg Arg Ile Phe Lys Ala Glu Glu Gly
             340                 345                 350

Asn Val Phe Val Ile Ala Asp Phe Ser Gln Ile Glu Leu Arg Ile Ala
             355                 360                 365

Ala Glu Tyr Val Asn Asp Glu Ser Met Ile Lys Val Phe Arg Glu Gly
             370                 375                 380

Arg Asp Met His Lys Tyr Thr Ala Ser Val Leu Leu Gly Lys Lys Glu
385                 390                 395                 400

Glu Glu Ile Thr Lys Glu Glu Arg Gln Leu Ala Lys Ala Val Asn Phe
                 405                 410                 415

Gly Leu Ile Tyr Gly Ile Ser Ala Lys Gly Leu Ala Glu Tyr Ala Tyr
             420                 425                 430

Ser Ser Tyr Gly Ile Ala Leu Ser Leu Ala Glu Ala Glu Lys Ile Arg
             435                 440                 445

Ala Arg Phe Phe Glu His Phe Arg Gly Phe Lys Asp Trp His Glu Arg
             450                 455                 460
```

```
Val Lys Lys Glu Leu Arg Glu Lys Gly Lys Ser Glu Gly Tyr Thr Leu
465                 470                 475                 480

Leu Gly Arg Arg Tyr Thr Ala His Thr Phe Pro Asp Ala Val Asn Tyr
                485                 490                 495

Pro Ile Gln Gly Thr Gly Ala Asp Leu Leu Lys Leu Ser Val Leu Ile
            500                 505                 510

Phe Asp Ala Glu Val Arg Arg Glu Asn Ile Lys Ala Arg Val Ile Asn
        515                 520                 525

Leu Val His Asp Glu Ile Val Val Glu Cys Pro Met Glu Glu Gly Glu
    530                 535                 540

Arg Thr Ala Glu Leu Leu Glu Arg Ala Met Lys Arg Ala Gly Gly Ile
545                 550                 555                 560

Ile Leu Lys Lys Val Pro Val Glu Val Glu Cys Val Ile Lys Glu Arg
                565                 570                 575

Trp Glu Lys Glu
            580

<210> SEQ ID NO 3
<211> LENGTH: 1461
<212> TYPE: DNA
<213> ORGANISM: Unknown
<220> FEATURE:
<223> OTHER INFORMATION: Uncultured newly isolated virus

<400> SEQUENCE: 3
gcggttggga cttggattac gaccttacaa aaacttggct ttacatatga agaacttgaa      60
gacaaggaag ttttagattt gctttcaata gcaagattag tattaccaga aagatttaaa    120
gagaatggtt ttagtttgga tgttgtgttg aaggaagtgt taggtattga ttataaattt    180
gataaaaaga caataagaaa aacatttaca ccgcttttga tgacacaaga acaattagag    240
tatatagcat ctgatgtaat ctacttgcca gctttaaaag agaaacttga tgaaaagttt    300
aataaaagac tatggctacc ttacatcttg gacatggaag caacaaaaat tttagcagaa    360
gtgtctaaca atggtatgcc atttcttaaa gaaaaagcaa agaagagct agcagatta    420 agcaaggaat tagaaggact tagaaaagag cttggtttta atccaaactc tccaaaagaa    480
actcaaaaag ttttaaacac accagataca agcgaagcaa ctctaatgaa gttgataatt    540
agtaattcaa gcaaaaaagc tattgctgaa aaagttattc aagcaagaaa aatacaaaaa    600
gtaatagcaa tgattaacaa gtaccttaac tatgatagag taaaaggcac attctggact    660
acaacagcgc catcaggtag aatgtcttgt gataaagaaa atttacaaca aataccaaga    720
agtataagat atttgtttgg ctttgatgaa aactcagata aaacattagt tatagcagat    780
tatccacaaa tagaactaag acttgcaggt gtgttatgga agagccaaa atttatccaa    840 gcattcaacg aaggcaagga cttacacaaa caaacagcaa gcataatata tggcattcct    900
tatgaagaag taaataaaga acaaagacaa atagcaaaat cagcaaattt tggacttatt    960
tatggcatgt cagttgaggg atttgctaac tattgcataa aaatggaat accaatggac    1020 actcaaacag ctcaacacat cgtaaattca ttctttaact tctatggtaa gatagctgaa   1080
aaacataaag aaggaaatct tatcattcaa tcacaaggca tagcagaagg ttatacttgg   1140
cttggtagaa gatatatagc tcaaagactt aacgactacc ttaactatca aatacaaggc   1200
tctggtgcag aactgcttaa aaaagctgta atggaaatca atccaaata tccttatatc   1260 aaaatagtaa atccttgtcca tgacgaaatt gtagtagagg cttacaagga tgatgcacaa   1320
gatatagcaa ggataatcaa gcaagaaatg gaaaatgctt gggaatggtg tattcaagaa   1380
```

```
gctcaaaagc ttggtgttga tttaacacct gttaagcttg aatgtgaaaa ccctacgata    1440
tcaaatgtat gggagaagta a                                              1461
```

<210> SEQ ID NO 4
<211> LENGTH: 486
<212> TYPE: PRT
<213> ORGANISM: Unknown
<220> FEATURE:
<223> OTHER INFORMATION: Uncultured newly isolated virus

<400> SEQUENCE: 4

```
Ala Val Gly Thr Trp Ile Thr Thr Leu Gln Lys Leu Gly Phe Thr Tyr
1               5                   10                  15

Glu Glu Leu Glu Asp Lys Glu Val Leu Asp Leu Leu Ser Ile Ala Arg
            20                  25                  30

Leu Val Leu Pro Glu Arg Phe Lys Glu Asn Gly Phe Ser Leu Asp Val
        35                  40                  45

Val Leu Lys Glu Val Leu Gly Ile Asp Tyr Lys Phe Asp Lys Lys Thr
    50                  55                  60

Ile Arg Lys Thr Phe Thr Pro Leu Leu Met Thr Gln Glu Gln Leu Glu
65                  70                  75                  80

Tyr Ile Ala Ser Asp Val Ile Tyr Leu Pro Ala Leu Lys Glu Lys Leu
                85                  90                  95

Asp Glu Lys Phe Asn Lys Arg Leu Trp Leu Pro Tyr Ile Leu Asp Met
            100                 105                 110

Glu Ala Thr Lys Ile Leu Ala Glu Val Ser Asn Asn Gly Met Pro Phe
        115                 120                 125

Leu Lys Glu Lys Ala Lys Glu Leu Ser Arg Leu Ser Lys Glu Leu
    130                 135                 140

Glu Gly Leu Arg Lys Glu Leu Gly Phe Asn Pro Asn Ser Pro Lys Glu
145                 150                 155                 160

Thr Gln Lys Val Leu Asn Thr Pro Asp Thr Ser Glu Ala Thr Leu Met
                165                 170                 175

Lys Leu Ile Ile Ser Asn Ser Ser Lys Lys Ala Ile Ala Glu Lys Val
            180                 185                 190

Ile Gln Ala Arg Lys Ile Gln Lys Val Ile Ala Met Ile Asn Lys Tyr
        195                 200                 205

Leu Asn Tyr Asp Arg Val Lys Gly Thr Phe Trp Thr Thr Thr Ala Pro
    210                 215                 220

Ser Gly Arg Met Ser Cys Asp Lys Glu Asn Leu Gln Gln Ile Pro Arg
225                 230                 235                 240

Ser Ile Arg Tyr Leu Phe Gly Phe Asp Glu Asn Ser Asp Lys Thr Leu
                245                 250                 255

Val Ile Ala Asp Tyr Pro Gln Ile Glu Leu Arg Leu Ala Gly Val Leu
            260                 265                 270

Trp Lys Glu Pro Lys Phe Ile Gln Ala Phe Asn Glu Gly Lys Asp Leu
        275                 280                 285

His Lys Gln Thr Ala Ser Ile Ile Tyr Gly Ile Pro Tyr Glu Glu Val
    290                 295                 300

Asn Lys Glu Gln Arg Gln Ile Ala Lys Ser Ala Asn Phe Gly Leu Ile
305                 310                 315                 320

Tyr Gly Met Ser Val Glu Gly Phe Ala Asn Tyr Cys Ile Lys Asn Gly
                325                 330                 335

Ile Pro Met Asp Thr Gln Thr Ala Gln His Ile Val Asn Ser Phe Phe
            340                 345                 350
```

Asn Phe Tyr Gly Lys Ile Ala Glu Lys His Lys Glu Gly Asn Leu Ile
            355                 360                 365

Ile Gln Ser Gln Gly Ile Ala Glu Gly Tyr Thr Trp Leu Gly Arg Arg
        370                 375                 380

Tyr Ile Ala Gln Arg Leu Asn Asp Tyr Leu Asn Tyr Gln Ile Gln Gly
385                 390                 395                 400

Ser Gly Ala Glu Leu Leu Lys Lys Ala Val Met Glu Ile Lys Ser Lys
                405                 410                 415

Tyr Pro Tyr Ile Lys Ile Val Asn Leu Val His Asp Glu Ile Val Val
            420                 425                 430

Glu Ala Tyr Lys Asp Asp Ala Gln Asp Ile Ala Arg Ile Ile Lys Gln
            435                 440                 445

Glu Met Glu Asn Ala Trp Glu Trp Cys Ile Gln Glu Ala Gln Lys Leu
        450                 455                 460

Gly Val Asp Leu Thr Pro Val Lys Leu Glu Cys Glu Asn Pro Thr Ile
465                 470                 475                 480

Ser Asn Val Trp Glu Lys
            485

<210> SEQ ID NO 5
<211> LENGTH: 1767
<212> TYPE: DNA
<213> ORGANISM: Unknown
<220> FEATURE:
<223> OTHER INFORMATION: Uncultured newly isolated virus

<400> SEQUENCE: 5

```
atgggagaag atgggctatc tttacctaag atgatgaata caccaaaacc aattcttaaa      60
cctcaaccaa aagctttagt agaaccagtg ctttgcgata gcattgatga ataccagcg     120
aaatataatg aaccagtata ctttgacttg gaaactgacg aagacagacc agttcttgca     180
agtatttatc aacctcactt tgaacgcaag gtgtattgtt taaacctctt gaaagaaaag     240
gtagcaaggt ttaaagactg gcttcttaaa ttctcagaaa taagaggatg gggtcttgac     300
tttgacttac gggttcttgg ctacacctac gaacaactta gaaacaagaa gattgtagat     360
gttcagcttg cgataaaagt ccagcactac gagagattta gcagggtgg gaccaaaggt     420
gaaggtttca gacttgatga tgtggcacga gatttgcttg gtatagaata tccgatgaac     480
aaaacaaaaa ttcgtgaaac cttcaaaaac aacatgtttc attcatttag caacgaacaa     540
cttctttatg cctcgcttga tgcatacata ccacacttgc tttacgaaca actaacatca     600
agcacgctta atagtcttgt ttatcagctt gatcaacagg cacagaaagt tgtgatagaa     660
acatcgcaac acggcatgcc agtaaaacta aaagcattag aagaagaaat acacagacta     720
actcagctac gcagtgaaat gcaaaagcag ataccattta actataactc tccaaaacaa     780
acggcaaaat tctttggagt aaatagttct tcaaaagatg tattgatgga cttagctcta     840
caaggaaatg aaatggctaa aaaggtgctt gaagcaagac aaatagaaaa atctcttgct     900
tttgcaaaag acctctatga tatagctaaa agaagtggtg gtagaattta cggcaacttc     960
tttactacaa cagcaccatc tggcagaatg tcttgctcgg atataaatct tcaacagata    1020
ccgcgtaggc ttagatcatt cataggcttt gatacagagg acaaaaagct tatcaccgca    1080
gactttccgc aaaattgagct tagacttgca ggtgtgattt ggaatgaacc taaattcata    1140
gaagcattta gcaaggtat agaccttcac aagcttacag catcaatact gtttgataag    1200
aacatagaag aagtaagcaa ggaagaaagg caaattggaa aatctgcgaa ttttgggctt    1260
```

```
atctatggta ttgcaccaaa aggtttcgca gaatattgta tagcgaacgg tattaacatg   1320
acagaagagc aggcatacga aataagtcag aaagtggaag aagtattaca caaagattgc   1380
agacaacatc aagtagcata tgaaaggttc aaatacaatg agtatgtaga taacgaaaca   1440
tggcttaaca gaacatatcg tgcatggaaa ccacaagacc tcttgaacta tcaaatacaa   1500
ggcagtggtg cggagctatt caagaaagct atagtattgt aaaagaaac aaagccagac    1560 ttgaagatag tcaatctcgt gcatgatgag atagtagtag aagcagatag caagaaagca   1620
caagacttgg ctaagctaat aaagagaaa atggaggaag cgtgggattg gtgtcttgaa    1680
aaagcagaag agtttggtaa tagagttgct aaaataaaac ttgaagtgga ggagccacat   1740
gtgggtaata catgggaaaa gccttga                                      1767
```

<210> SEQ ID NO 6
<211> LENGTH: 588
<212> TYPE: PRT
<213> ORGANISM: Unknown
<220> FEATURE:
<223> OTHER INFORMATION: Uncultured newly isolated virus

<400> SEQUENCE: 6

```
Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
            20                  25                  30

Asp Ser Ile Asp Glu Ile Pro Ala Lys Tyr Asn Glu Pro Val Tyr Phe
        35                  40                  45

Asp Leu Glu Thr Asp Glu Asp Arg Pro Val Leu Ala Ser Ile Tyr Gln
    50                  55                  60

Pro His Phe Glu Arg Lys Val Tyr Cys Leu Asn Leu Lys Glu Lys
65                  70                  75                  80

Val Ala Arg Phe Lys Asp Trp Leu Leu Lys Phe Ser Glu Ile Arg Gly
                85                  90                  95

Trp Gly Leu Asp Phe Asp Leu Arg Val Leu Gly Tyr Thr Tyr Glu Gln
            100                 105                 110

Leu Arg Asn Lys Lys Ile Val Asp Val Gln Leu Ala Ile Lys Val Gln
        115                 120                 125

His Tyr Glu Arg Phe Lys Gln Gly Gly Thr Lys Gly Glu Gly Phe Arg
    130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
            180                 185                 190

Leu Leu Tyr Glu Gln Leu Thr Ser Ser Thr Leu Asn Ser Leu Val Tyr
        195                 200                 205

Gln Leu Asp Gln Gln Ala Gln Lys Val Val Ile Glu Thr Ser Gln His
    210                 215                 220

Gly Met Pro Val Lys Leu Lys Ala Leu Glu Glu Ile His Arg Leu
225                 230                 235                 240

Thr Gln Leu Arg Ser Glu Met Gln Lys Gln Ile Pro Phe Asn Tyr Asn
                245                 250                 255

Ser Pro Lys Gln Thr Ala Lys Phe Phe Gly Val Asn Ser Ser Ser Lys
            260                 265                 270

Asp Val Leu Met Asp Leu Ala Leu Gln Gly Asn Glu Met Ala Lys Lys
```

275                 280                 285
Val Leu Glu Ala Arg Gln Ile Glu Lys Ser Leu Ala Phe Ala Lys Asp
290                 295                 300

Leu Tyr Asp Ile Ala Lys Arg Ser Gly Gly Arg Ile Tyr Gly Asn Phe
305                 310                 315                 320

Phe Thr Thr Thr Ala Pro Ser Gly Arg Met Ser Cys Ser Asp Ile Asn
                325                 330                 335

Leu Gln Gln Ile Pro Arg Arg Leu Arg Ser Phe Ile Gly Phe Asp Thr
                340                 345                 350

Glu Asp Lys Lys Leu Ile Thr Ala Asp Phe Pro Gln Ile Glu Leu Arg
            355                 360                 365

Leu Ala Gly Val Ile Trp Asn Glu Pro Lys Phe Ile Glu Ala Phe Arg
370                 375                 380

Gln Gly Ile Asp Leu His Lys Leu Thr Ala Ser Ile Leu Phe Asp Lys
385                 390                 395                 400

Asn Ile Glu Glu Val Ser Lys Gly Glu Arg Gln Ile Gly Lys Ser Ala
                405                 410                 415

Asn Phe Gly Leu Ile Tyr Gly Ile Ala Pro Lys Gly Phe Ala Glu Tyr
                420                 425                 430

Cys Ile Ala Asn Gly Ile Asn Met Thr Glu Glu Gln Ala Tyr Glu Ile
            435                 440                 445

Ser Gln Lys Val Glu Glu Val Leu His Lys Asp Cys Arg Gln His Gln
450                 455                 460

Val Ala Tyr Glu Arg Phe Lys Tyr Asn Glu Tyr Val Asp Asn Glu Thr
465                 470                 475                 480

Trp Leu Asn Arg Thr Tyr Arg Ala Trp Lys Pro Gln Asp Leu Leu Asn
                485                 490                 495

Tyr Gln Ile Gln Gly Ser Gly Ala Glu Leu Phe Lys Lys Ala Ile Val
                500                 505                 510

Leu Leu Lys Glu Thr Lys Pro Asp Leu Lys Ile Val Asn Leu Val His
            515                 520                 525

Asp Glu Ile Val Val Glu Ala Asp Ser Lys Glu Ala Gln Asp Leu Ala
530                 535                 540

Lys Leu Ile Lys Glu Lys Met Glu Glu Ala Trp Asp Trp Cys Leu Glu
545                 550                 555                 560

Lys Ala Glu Glu Phe Gly Asn Arg Val Ala Lys Ile Lys Leu Glu Val
                565                 570                 575

Glu Glu Pro His Val Gly Asn Thr Trp Glu Lys Pro
            580                 585

<210> SEQ ID NO 7
<211> LENGTH: 2250
<212> TYPE: DNA
<213> ORGANISM: Unknown
<220> FEATURE:
<223> OTHER INFORMATION: Uncultured newly isolated virus

<400> SEQUENCE: 7
atggggcttg atcaaatact tgatatgagc tacttcgttg actcgggggc aacaatgctc      60
aagctcatac tcagagggag cggagggaag aatgttgtaa cagtgccagc acccttcaac     120
ccatacttct tcataaagaa gagagacctg atagggctc aaagcatact ccccgactac      180
gcaagagtag aggatgctga cgccattact gctgaagggg agcgggttgt gaagataagt     240
gttccaacgc cacccctggt tagagttgtg agagagaaac tccacgagga aggtatagag     300
tcgtacgagg ctgacatccc ttacacccgg agggtcatga tagacctgga tttaaaggtg     360

```
gcgtacccccg agacagtggc tgctttcgac atagaggttg acgcaacaaa ggggttcccc      420
gatatcaaca acccgcagtc tagggtcctg tctatctccg tgtacgacgg gagcgaggag      480
atattcctat gctcagacga tgagatcgag atgttcaagg agttcaacaa gctcctgaga      540
aagtatgatg tgctgatagg ctggaactca gctgcattcg actacccttca cctagttgag     600
agagctaagg tgctcggata ctacgtggac gaggagatgt ccagcacgt ggacatattc       660
gggatattcc agacctactt caagagagag atgagcgact tcaagctcaa aaccgttgcc      720
ctcaaagtcc tgggatccaa ggtgccactt ggcgccctgc tggatttcga gaggcctgga     780
gacataagga agctcacaga gttcttcgag aagcgcaggg atctcttgaa gctatacaac     840
atggatcaga ctaaggctat atggatgata acagcgagt caggtgtgct ccaaacatac      900
atcactcagg ccaggctcgc taacataata ccttggcacc gggtctctcc gagaacagat     960
agctcacagg agtacatatc ctacaacaat gattgtcgag accttgtgct gaagaaagct    1020
ctagctcaca gcccaggat agttttccca tctaagaaga acggtgagaa cgaagactgg     1080
gatgaggatg caaaggagag cacatacact ggagcaatag tcttcaaccc gattccaggg    1140
ctatgggaga atgttgtgct cctggacttc gcttcgatgt accctagggt tataatgacg    1200
ttcaacatct catacgacac ctggaccccct aaccctggtg aaaacgatat tcttgcgccc   1260
cacggtggat tcatcacctc tagagagggg ttccttccaa cggtgctaag ggagcttgag    1320
gggtacagga gtctagctaa gaagatggtt gacgcatatg agccaggtga cccccatgagg  1380
gtcatatgga acgcaaggca gttcgcattc aaactcatac tggtttcagc gtacggtgta    1440
gctggattca ggcactctag actctacagg gttgagatag ctgagagcat cacagggtac   1500
acgagagacg caataatgaa ggccagagag gtgatagaga ggcacggttg gagggtcctc    1560
tacggggaca ccgacagcct gttcttgtac aaccccaaga tcacaagcgt ggagaaggct    1620
tcagaggttg catcaagcga gctgctccca gccataaact cctttataag agactacgtg    1680
gtggagagat ggagggtccc gaggagcagg gttgtgttgg agttcaaggt tgacagggtg    1740
tactcgaagc tgaagctgct gagtgtgaag aagaggtact atggcttggt tgcgtgggag    1800
gagaggatgc tcgagcaacc ctacattcag atcaagggcc tggaagcaag agaggtgat    1860
tggcctgacc tggtcaagga gatacagtca gaggtgatca agctgtacct cctagaggga   1920
cccatagctg tagacaggta tctgaaggag atgaagagga agctcctgtc cggggagata  1980
cccctggaga agctggttat caagaagcat ctgaacaaga ggcttgacga gtataagcat    2040
aacgcgcccc actacagggc tgcaaggaag ctcctagaga tgaggttccc cgttagaacc   2100
ggggatagaa tagagttcat ctaccttgac gacaaggtga tccccatggt tccagggctg   2160
aagctatcag aggttgacct gaagaagtgg tggaggaaat acgttgtccc ggtagtcgag   2220
agactggaga tagagagcag agggagctag                                    2250
```

<210> SEQ ID NO 8
<211> LENGTH: 749
<212> TYPE: PRT
<213> ORGANISM: Unknown
<220> FEATURE:
<223> OTHER INFORMATION: Uncultured newly isolated virus

<400> SEQUENCE: 8

Met Gly Leu Asp Gln Ile Leu Asp Met Ser Tyr Phe Val Asp Ser Gly
1               5                   10                  15

Ala Thr Met Leu Lys Leu Ile Leu Arg Gly Ser Gly Gly Lys Asn Val
            20                  25                  30

```
Val Thr Val Pro Ala Pro Phe Asn Pro Tyr Phe Phe Ile Lys Lys Arg
        35                  40                  45

Asp Leu Asp Arg Ala Gln Ser Ile Leu Pro Asp Tyr Ala Arg Val Glu
        50                  55                  60

Asp Ala Asp Ala Ile Thr Ala Glu Gly Glu Arg Val Val Lys Ile Ser
65                  70                  75                  80

Val Pro Thr Pro Pro Leu Val Arg Val Val Arg Glu Lys Leu His Glu
                85                  90                  95

Glu Gly Ile Glu Ser Tyr Glu Ala Asp Ile Pro Tyr Thr Arg Arg Val
                100                 105                 110

Met Ile Asp Leu Asp Leu Lys Val Ala Tyr Pro Glu Thr Val Ala Ala
        115                 120                 125

Phe Asp Ile Glu Val Asp Ala Thr Lys Gly Phe Pro Asp Ile Asn Asn
        130                 135                 140

Pro Gln Ser Arg Val Leu Ser Ile Ser Val Tyr Asp Gly Ser Glu Glu
145                 150                 155                 160

Ile Phe Leu Cys Ser Asp Asp Glu Ile Glu Met Phe Lys Glu Phe Asn
                165                 170                 175

Lys Leu Leu Arg Lys Tyr Asp Val Leu Ile Gly Trp Asn Ser Ala Ala
                180                 185                 190

Phe Asp Tyr Pro Tyr Leu Val Glu Arg Ala Lys Val Leu Gly Tyr Tyr
                195                 200                 205

Val Asp Glu Glu Met Phe Gln His Val Asp Ile Phe Gly Ile Phe Gln
210                 215                 220

Thr Tyr Phe Lys Arg Glu Met Ser Asp Phe Lys Leu Lys Thr Val Ala
225                 230                 235                 240

Leu Lys Val Leu Gly Ser Lys Val Pro Leu Gly Ala Leu Leu Asp Phe
                245                 250                 255

Glu Arg Pro Gly Asp Ile Arg Lys Leu Thr Glu Phe Phe Glu Lys Arg
                260                 265                 270

Arg Asp Leu Leu Lys Leu Tyr Asn Met Asp Gln Thr Lys Ala Ile Trp
                275                 280                 285

Met Ile Asn Ser Glu Ser Gly Val Leu Gln Thr Tyr Ile Thr Gln Ala
        290                 295                 300

Arg Leu Ala Asn Ile Ile Pro Trp His Arg Val Ser Pro Arg Thr Asp
305                 310                 315                 320

Ser Ser Gln Glu Tyr Ile Ser Tyr Asn Asn Asp Cys Arg Asp Leu Val
                325                 330                 335

Leu Lys Lys Ala Leu Ala His Lys Pro Arg Ile Val Phe Pro Ser Lys
                340                 345                 350

Lys Asn Gly Glu Asn Glu Asp Trp Asp Glu Asp Ala Lys Glu Ser Thr
                355                 360                 365

Tyr Thr Gly Ala Ile Val Phe Asn Pro Ile Pro Gly Leu Trp Glu Asn
        370                 375                 380

Val Val Leu Leu Asp Phe Ala Ser Met Tyr Pro Arg Val Ile Met Thr
385                 390                 395                 400

Phe Asn Ile Ser Tyr Asp Thr Trp Thr Pro Asn Pro Gly Glu Asn Asp
                405                 410                 415

Ile Leu Ala Pro His Gly Gly Phe Ile Thr Ser Arg Glu Gly Phe Leu
                420                 425                 430

Pro Thr Val Leu Arg Glu Leu Glu Gly Tyr Arg Ser Leu Ala Lys Lys
        435                 440                 445

Met Val Asp Ala Tyr Glu Pro Gly Asp Pro Met Arg Val Ile Trp Asn
```

-continued

```
            450                455                460
Ala Arg Gln Phe Ala Phe Lys Leu Ile Leu Val Ser Ala Tyr Gly Val
465                 470                 475                 480

Ala Gly Phe Arg His Ser Arg Leu Tyr Arg Val Glu Ile Ala Glu Ser
                485                 490                 495

Ile Thr Gly Tyr Thr Arg Asp Ala Ile Met Lys Ala Arg Glu Val Ile
            500                 505                 510

Glu Arg His Gly Trp Arg Val Leu Tyr Gly Asp Thr Asp Ser Leu Phe
        515                 520                 525

Leu Tyr Asn Pro Lys Ile Thr Ser Val Glu Lys Ala Ser Glu Val Ala
530                 535                 540

Ser Ser Glu Leu Leu Pro Ala Ile Asn Ser Phe Ile Arg Asp Tyr Val
545                 550                 555                 560

Val Glu Arg Trp Arg Val Pro Arg Ser Arg Val Val Leu Glu Phe Lys
                565                 570                 575

Val Asp Arg Val Tyr Ser Lys Leu Lys Leu Leu Ser Val Lys Lys Arg
            580                 585                 590

Tyr Tyr Gly Leu Val Ala Trp Glu Glu Arg Met Leu Glu Gln Pro Tyr
        595                 600                 605

Ile Gln Ile Lys Gly Leu Glu Ala Arg Arg Gly Asp Trp Pro Asp Leu
    610                 615                 620

Val Lys Glu Ile Gln Ser Glu Val Ile Lys Leu Tyr Leu Leu Glu Gly
625                 630                 635                 640

Pro Ile Ala Val Asp Arg Tyr Leu Lys Glu Met Lys Arg Lys Leu Leu
                645                 650                 655

Ser Gly Glu Ile Pro Leu Glu Lys Leu Val Ile Lys Lys His Leu Asn
            660                 665                 670

Lys Arg Leu Asp Glu Tyr Lys His Asn Ala Pro His Tyr Arg Ala Ala
        675                 680                 685

Arg Lys Leu Leu Glu Met Arg Phe Pro Val Arg Thr Gly Asp Arg Ile
    690                 695                 700

Glu Phe Ile Tyr Leu Asp Asp Lys Val Ile Pro Met Val Pro Gly Leu
705                 710                 715                 720

Lys Leu Ser Glu Val Asp Leu Lys Lys Trp Trp Arg Lys Tyr Val Val
                725                 730                 735

Pro Val Val Glu Arg Leu Glu Ile Glu Ser Arg Gly Ser
            740                 745
```

<210> SEQ ID NO 9
<211> LENGTH: 1992
<212> TYPE: DNA
<213> ORGANISM: Unknown
<220> FEATURE:
<223> OTHER INFORMATION: Uncultured newly isolated virus

<400> SEQUENCE: 9

```
atgatagacc tggatttaaa agtagcgtac ccagagactg tagctgcttt cgacatagag    60
gttgacgcaa caaagggggtt ccccgatatc aacaacccccc agtctagagt cctgtctatc   120
tcagtgtacg atgggagcga agagatattc ctatgctcag acgatgaggt cgagatgttc   180
aaggagttca caggctcct gaggaagtat gatgtgatga tagggtggaa ctcagctgca   240
ttcgactacc cttacctcgt agagagagct aagatgctcg gatactacgt agacgaggag   300
atgttccagc acgtggacat attcgggata ttccagacct acttcaagag ggagatgagc   360
gacttcaagc tcaaaacagt tgccctcaag gtcctcggat ccaaggtgcc acttggcggc   420
```

-continued

```
cctgttggat ttcgagaggc caggggacat agctaagctc acggagttct tgagaggcg     480 cagggatctc ttgagactct acaacatgga tcagaccagg cgatatggat gataaacagc    540
gagtcaggcg tgctccagac ctacatcaca caggctaggc tcaccaacat aataacctgg    600
cacagggacc tctctgagaa gcagatagct cacaggaagt atatatccta caacaggatg    660
gtcgagaacc ttgtcttgaa gaaagctcta gctcacaagc cgaggatagt gttcccatcc    720
aagaagaacg gcgagaacaa cgagtgggat gaagacaata agagagctc atacacagga    780 gctatagtct tcaaccccgt gccagggcta tgggagaacg ttgtcctcct ggacttcgca    840
accatgtacc ctagggtcat aatgacattc aacatctcat acgacacctg accccgaac    900 cccggtgaga gcgatattct tgcgccccac ggtggattca tcacctctag agagggttc    960 cttccaacag tgctaaggga gcttgagggg tacaggagtc tagctaagaa gatggttgac   1020
gcatatgagc caggtgaccc catgagagtt atatggaatg caagacagtt cgcgttcaaa   1080
ctcatactgg tttcagcgta cggtgtagct ggattcaggc actctaggct ctacaggggtt   1140 gagatagccg agagcatcac tgggtacacc agagacgcaa taatgaaggc gagagaggtg   1200
atagagagtc acggttggag ggtcctctac ggtgacactg acagcctgtt cttgtacaac   1260 cccgggtct cgagcgctga gaaggctgca gaggttgcat caagcgagct acttccagcc    1320
ataaactcct ttataagaga ctacgctgtg gagagatgga gggttccgag agcagggtt    1380 gtgttggagt tcaaggatga cagggtgtac tcaaagctga agctcctgag tgtgaagaag    1440
aggtactatg gcttggtatc gtgggaggag aggatgctcg agaaacccta cattcagatc    1500
aagggccttg aggctaggag gggtgattgg cctgacctgg tcaaggagat acagtcagag    1560
gtgatcaagc tgtacctcct agagggccca gagctgttg actcgtatct caaggagatg    1620
aagaggaagc tcctatcggg ggagataccc ttggagaagc tggttatcaa gaagcacctg    1680
aacaagaggc tgggcgagat aagcataatg cgccccacta ccagggctgc caggaagctc    1740
ctagagatga ggttccccgt tagaacaggg gatagaatag agttcatcta ccttgacgac    1800
aaggtgatcc ccatggttcc agggctgaag cttcagagg ttgacctgag gaagtggtgg    1860
aggaaatacg ttgtcccagt agtggagaga ctggagatag agagcagagg gagcttgcta    1920
gacaggatgc ggccgcttgt atctgatacg acattcagga tccgaattcg tcgacgatat   1980
cttcccctat ag                                                        1992
```

<210> SEQ ID NO 10
<211> LENGTH: 661
<212> TYPE: PRT
<213> ORGANISM: Unknown
<220> FEATURE:
<223> OTHER INFORMATION: Uncultured newly isolated virus

<400> SEQUENCE: 10

```
Met Ile Asp Leu Asp Leu Lys Val Ala Tyr Pro Glu Thr Val Ala Ala
1               5                   10                  15

Phe Asp Ile Glu Val Asp Ala Thr Lys Gly Phe Pro Asp Ile Asn Asn
            20                  25                  30

Pro Gln Ser Arg Val Leu Ser Ile Ser Val Tyr Asp Gly Ser Glu Glu
        35                  40                  45

Ile Phe Leu Cys Ser Asp Asp Glu Val Glu Met Phe Lys Glu Phe Asn
    50                  55                  60

Arg Leu Leu Arg Lys Tyr Asp Val Met Ile Gly Trp Asn Ser Ala Ala
65                  70                  75                  80

Phe Asp Tyr Pro Tyr Leu Val Glu Arg Ala Lys Met Leu Gly Tyr Tyr
```

-continued

```
                     85                    90                    95
Val Asp Glu Glu Met Phe Gln His Val Asp Ile Phe Gly Ile Phe Gln
                    100                   105                   110

Thr Tyr Phe Lys Arg Glu Met Ser Asp Phe Lys Leu Lys Thr Val Ala
                    115                   120                   125

Leu Lys Val Leu Gly Ser Lys Val Pro Leu Gly Gly Pro Val Gly Phe
                    130                   135             140

Arg Glu Ala Arg Gly His Ser Ala His Gly Val Leu Glu Ala Gln Gly
145                           150                   155             160

Ser Leu Glu Thr Leu Gln His Gly Ser Asp Gln Ala Ile Trp Met Ile
                    165                   170                   175

Asn Ser Glu Ser Gly Val Leu Gln Thr Tyr Ile Thr Gln Ala Arg Leu
                    180                   185                   190

Thr Asn Ile Ile Thr Trp His Arg Asp Leu Ser Glu Lys Gln Ile Ala
                    195                   200                   205

His Arg Lys Tyr Ile Ser Tyr Asn Arg Met Val Glu Asn Leu Val Leu
                    210                   215                   220

Lys Lys Ala Leu Ala His Lys Pro Arg Ile Val Phe Pro Ser Lys Lys
225                           230                   235             240

Asn Gly Glu Asn Asn Glu Trp Asp Glu Asp Asn Lys Glu Ser Ser Tyr
                    245                   250                   255

Thr Gly Ala Ile Val Phe Asn Pro Pro Gly Leu Trp Glu Asn Val
                    260                   265                   270

Val Leu Leu Asp Phe Ala Thr Met Tyr Pro Arg Val Ile Met Thr Phe
                    275                   280                   285

Asn Ile Ser Tyr Asp Thr Trp Thr Pro Asn Pro Gly Glu Ser Asp Ile
                    290                   295                   300

Leu Ala Pro His Gly Gly Phe Ile Thr Ser Arg Glu Gly Phe Leu Pro
305                           310                   315             320

Thr Val Leu Arg Glu Leu Glu Gly Tyr Arg Ser Leu Ala Lys Lys Met
                    325                   330                   335

Val Asp Ala Tyr Glu Pro Gly Asp Pro Met Arg Val Ile Trp Asn Ala
                    340                   345                   350

Arg Gln Phe Ala Phe Lys Leu Ile Leu Val Ser Ala Tyr Gly Val Ala
                    355                   360                   365

Gly Phe Arg His Ser Arg Leu Tyr Arg Val Glu Ile Ala Glu Ser Ile
                    370                   375                   380

Thr Gly Tyr Thr Arg Asp Ala Ile Met Lys Ala Arg Glu Val Ile Glu
385                           390                   395             400

Ser His Gly Trp Arg Val Leu Tyr Gly Asp Thr Asp Ser Leu Phe Leu
                    405                   410                   415

Tyr Asn Pro Gly Val Ser Ser Ala Glu Lys Ala Ala Glu Val Ala Ser
                    420                   425                   430

Ser Glu Leu Leu Pro Ala Ile Asn Ser Phe Ile Arg Asp Tyr Ala Val
                    435                   440                   445

Glu Arg Trp Arg Val Pro Arg Ser Arg Val Leu Glu Phe Lys Asp
                    450                   455                   460

Asp Arg Val Tyr Ser Lys Leu Lys Leu Leu Ser Val Lys Lys Arg Tyr
465                           470                   475             480

Tyr Gly Leu Val Ser Trp Glu Glu Arg Met Leu Glu Lys Pro Tyr Ile
                    485                   490                   495

Gln Ile Lys Gly Leu Glu Ala Arg Gly Asp Trp Pro Asp Leu Val
                    500                   505                   510
```

```
Lys Glu Ile Gln Ser Glu Val Ile Lys Leu Tyr Leu Leu Glu Gly Pro
        515                 520                 525
Arg Ala Val Asp Ser Tyr Leu Lys Glu Met Lys Arg Lys Leu Leu Ser
    530                 535                 540
Gly Glu Ile Pro Leu Glu Lys Leu Val Ile Lys Lys His Leu Asn Lys
545                 550                 555                 560
Arg Leu Gly Glu Ile Ser Ile Met Arg Pro Thr Thr Arg Ala Ala Arg
                565                 570                 575
Lys Leu Leu Glu Met Arg Phe Pro Val Arg Thr Gly Asp Arg Ile Glu
            580                 585                 590
Phe Ile Tyr Leu Asp Asp Lys Val Ile Pro Met Val Pro Gly Leu Lys
        595                 600                 605
Leu Ser Glu Val Asp Leu Arg Lys Trp Trp Arg Lys Tyr Val Val Pro
    610                 615                 620
Val Val Glu Arg Leu Glu Ile Glu Ser Arg Gly Ser Leu Leu Asp Arg
625                 630                 635                 640
Met Arg Pro Leu Val Ser Asp Thr Thr Phe Arg Ile Arg Ile Arg Arg
                645                 650                 655
Arg Tyr Leu Pro Leu
            660

<210> SEQ ID NO 11
<211> LENGTH: 591
<212> TYPE: DNA
<213> ORGANISM: Unknown
<220> FEATURE:
<223> OTHER INFORMATION: Uncultured newly isolated virus

<400> SEQUENCE: 11
atgcactggt ctctcttaga tgagtacctt aactctggag cgataaggat gagcgagggg      60
tccatggagt cagtcgcata catagaggtt gcaaagaaga tactctactg cagaaagtgc     120
ggtttcaatg tgaagcaccc ataccccgga tccggctcgt tggatgcaaa gataatgata     180
gttgggagag cccctcaccc cacaggaag tcatttgaga acttctcgga gaggagcagg      240
gaggttgttg atgctgttct atctgcactg ggtctatcca gggagacagt gtacatgact     300
aacgctgtga agtgtcctct ctaccatctg gagatggagg acaggatgaa gtacattgac     360
ttatgcttcg agcacctgct aagcgagata cagattgtga aacctaagat cgttatcagc     420
ttcggtgtca tagctgagag agctgttttcc aaggcattga gggttagcac acataagttc     480
ttccatgtag ctctaccca tccgatgaaa gtggtgtatg ccagatgac gctggaagac      540 taccttaggg aggtgaagag gagatggggc ttgatcaaat acttgatata a              591

<210> SEQ ID NO 12
<211> LENGTH: 196
<212> TYPE: PRT
<213> ORGANISM: Unknown
<220> FEATURE:
<223> OTHER INFORMATION: Uncultured newly isolated virus

<400> SEQUENCE: 12

Met His Trp Ser Leu Leu Asp Glu Tyr Leu Asn Ser Gly Ala Ile Arg
1               5                   10                  15
Met Ser Glu Gly Ser Met Glu Ser Val Ala Tyr Ile Glu Val Ala Lys
            20                  25                  30
Lys Ile Leu Tyr Cys Arg Lys Cys Gly Phe Asn Val Lys His Pro Tyr
        35                  40                  45
Pro Gly Ser Gly Ser Leu Asp Ala Lys Ile Met Ile Val Gly Glu Ser
```

```
                50                55                60
Pro Ser Pro His Arg Lys Ser Phe Glu Asn Phe Ser Glu Arg Ser Arg
65                  70                  75                  80

Glu Val Val Asp Ala Val Leu Ser Ala Leu Gly Leu Ser Arg Glu Thr
                85                  90                  95

Val Tyr Met Thr Asn Ala Val Lys Cys Pro Leu Tyr His Leu Glu Met
            100                 105                 110

Glu Asp Arg Met Lys Tyr Ile Asp Leu Cys Phe Glu His Leu Leu Ser
        115                 120                 125

Glu Ile Gln Ile Val Lys Pro Lys Ile Val Ser Phe Gly Val Ile
    130                 135                 140

Ala Glu Arg Ala Val Ser Lys Ala Leu Arg Val Ser Thr His Lys Phe
145                 150                 155                 160

Phe His Val Ala Leu Pro His Pro Met Lys Val Val Tyr Gly Gln Met
                165                 170                 175

Thr Leu Glu Asp Tyr Leu Arg Glu Val Lys Arg Arg Trp Gly Leu Ile
            180                 185                 190

Lys Tyr Leu Ile
        195

<210> SEQ ID NO 13
<211> LENGTH: 1029
<212> TYPE: DNA
<213> ORGANISM: Unknown
<220> FEATURE:
<223> OTHER INFORMATION: Uncultured newly isolated virus

<400> SEQUENCE: 13
atgcaaaaag aaataccatt taactacaat tcacctaaac aaacagcaaa gcttttggt      60
atagatagtt cttcaaaaga tgtgcttatg gatttagcat taaggggtaa tgaggtagct    120
aagaaagttc ttgaagcaag acaaatagaa aagtctttag cttttgcaaa agacctttat    180
gatatagcta aaagaatgg tggtagaatt cacggaaact tctttactac taccgcacca    240
tcgggtagaa tgtcttgttc agatataaac ttacaacaaa tacctcgcag gttaagacaa    300
ttcataggtt ttgaaacaga agataaaaaa cttataactg ctgactttcc tcaaatagaa    360
cttaggcttg cgggtgtaat gtggaatgaa ccagaatttt taaaagcgtt tagggatggt    420
atagacttac ataaactaac agcttcaatc ctgtttgata aaaaaattaa tgaggtaagt    480
aaagaagaaa gacaaatagg caaatcagca aactttggtt taatttacgg tatctctcca    540
aagggttttg ctgaatattg tataagcaac ggaataaata acagaagaa aatggctatt    600
gagattgtaa agaaatggaa gaagttttac agaaaaatag cagaacaaca ccaactggct    660
tacgaaaggt tcaagtatgc tgaatttgta gataatgaaa catggttgaa tagaccttac    720
agggcttata aacctcagga ccttctcaat tatcaaattc aaggaagcgg tgctgagttg    780
tttaaaaaag ctataattct acttaaagaa acaaaaccag accttaagct tgtaaatctt    840
gtgcatgatg agattgtagt ggaaacctca acagaagaag ctgaagatat agctttgttg    900
gtaaaacaaa gatggaaga ggcttgggat tattgtttag aaaaggctaa ggaatttggt    960
aataatgtgg cggatataaa acttgaagta gaaaaaccta acataagcag tgtatgggaa   1020
aaggagtaa                                                           1029

<210> SEQ ID NO 14
<211> LENGTH: 342
<212> TYPE: PRT
<213> ORGANISM: Unknown
```

<220> FEATURE:
<223> OTHER INFORMATION: Uncultured newly isolated virus

<400> SEQUENCE: 14

| | | | | | | | | | | | | | | |
|---|---|---|---|---|---|---|---|---|---|---|---|---|---|---|
| Met<br>1 | Gln | Lys | Glu | Ile<br>5 | Pro | Phe | Asn | Tyr | Asn<br>10 | Ser | Pro | Lys | Gln | Thr<br>15 | Ala |
| Lys | Leu | Phe | Gly<br>20 | Ile | Asp | Ser | Ser | Lys<br>25 | Asp | Val | Leu | Met<br>30 | Asp | Leu |
| Ala | Leu | Arg<br>35 | Gly | Asn | Glu | Val | Ala<br>40 | Lys | Val | Leu | Glu<br>45 | Ala | Arg | Gln |
| Ile | Glu<br>50 | Lys | Ser | Leu | Ala | Phe<br>55 | Ala | Lys | Asp | Leu | Tyr<br>60 | Asp | Ile | Ala | Lys |
| Lys<br>65 | Asn | Gly | Gly | Arg | Ile<br>70 | His | Gly | Asn | Phe | Phe<br>75 | Thr | Thr | Thr | Ala | Pro<br>80 |
| Ser | Gly | Arg | Met | Ser<br>85 | Cys | Ser | Asp | Ile | Asn<br>90 | Leu | Gln | Gln | Ile | Pro<br>95 | Arg |
| Arg | Leu | Arg | Gln<br>100 | Phe | Ile | Gly | Phe | Glu<br>105 | Thr | Glu | Asp | Lys | Lys<br>110 | Leu | Ile |
| Thr | Ala | Asp<br>115 | Phe | Pro | Gln | Ile | Glu<br>120 | Leu | Arg | Leu | Ala | Gly<br>125 | Val | Met | Trp |
| Asn | Glu<br>130 | Pro | Glu | Phe | Leu | Lys<br>135 | Ala | Phe | Arg | Asp | Gly<br>140 | Ile | Asp | Leu | His |
| Lys<br>145 | Leu | Thr | Ala | Ser | Ile<br>150 | Leu | Phe | Asp | Lys | Lys<br>155 | Ile | Asn | Glu | Val | Ser<br>160 |
| Lys | Glu | Glu | Arg | Gln<br>165 | Ile | Gly | Lys | Ser | Ala<br>170 | Asn | Phe | Gly | Leu | Ile<br>175 | Tyr |
| Gly | Ile | Ser | Pro<br>180 | Lys | Gly | Phe | Ala | Glu<br>185 | Tyr | Cys | Ile | Ser | Asn<br>190 | Gly | Ile |
| Asn | Ile | Thr<br>195 | Glu | Glu | Met | Ala | Ile<br>200 | Glu | Ile | Val | Lys | Lys<br>205 | Trp | Lys | Lys |
| Phe | Tyr<br>210 | Arg | Lys | Ile | Ala | Glu<br>215 | Gln | His | Gln | Leu | Ala<br>220 | Tyr | Glu | Arg | Phe |
| Lys<br>225 | Tyr | Ala | Glu | Phe | Val<br>230 | Asp | Asn | Glu | Thr | Trp<br>235 | Leu | Asn | Arg | Pro | Tyr<br>240 |
| Arg | Ala | Tyr | Lys | Pro<br>245 | Gln | Asp | Leu | Leu | Asn<br>250 | Tyr | Gln | Ile | Gln | Gly<br>255 | Ser |
| Gly | Ala | Glu | Leu<br>260 | Phe | Lys | Lys | Ala | Ile<br>265 | Ile | Leu | Leu | Lys<br>270 | Glu | Thr | Lys |
| Pro | Asp<br>275 | Leu | Lys | Leu | Val | Asn<br>280 | Leu | Val | His | Asp | Glu<br>285 | Ile | Val | Val | Glu |
| Thr | Ser<br>290 | Thr | Glu | Glu | Ala | Glu<br>295 | Asp | Ile | Ala | Leu | Leu<br>300 | Val | Lys | Gln | Lys |
| Met<br>305 | Glu | Glu | Ala | Trp | Asp<br>310 | Tyr | Cys | Leu | Glu | Lys<br>315 | Ala | Lys | Glu | Phe | Gly<br>320 |
| Asn | Asn | Val | Ala | Asp<br>325 | Ile | Lys | Leu | Glu | Val<br>330 | Lys | Pro | Asn | Ile<br>335 | Ser |
| Ser | Val | Trp | Glu | Lys<br>340 | Glu | | | | | | | | | |

<210> SEQ ID NO 15
<211> LENGTH: 2253
<212> TYPE: DNA
<213> ORGANISM: Unknown
<220> FEATURE:
<223> OTHER INFORMATION: Uncultured newly isolated virus

<400> SEQUENCE: 15

```
atgagctact tcgttgactc aggggcaaca atgctcaagc tcatactcag ggggagcgga      60
ggtaagaagg ttgtaacagt gccagccccc ttcaacccat acttttttcat aaagaagaga    120 gacctggata gggctcaaag catactccca gtacttacgc ttagcgtgga ggatgctgac    180
gccattacag ctgaagggga gagggttgtg aagataagtg ttccaacgcc acccctggtc    240
agggttgtga gggagaaact ccacgaggag gggatagagt cgtacgaggc tgatatccct    300
tacaccagga gggtcatgat agacctggat ttaaaggttg cgtaccctga gaccgttgca    360
gctttcgaca tagaggttga cgcaacaagg gggttccccg atatcaacaa cccgcagtca    420
agggttctct ctatctccgt gtacgacggg agcgaggaga tattcctatg ctcagacgat    480
gagatcgaga tgttcaagga gttcaacaag ctcctgagga ggtacgatgt gctgataggc    540
tggaactcag ctgcattcga ctaccttac ctagtagaga gagcaaaggt gctcggatac     600
tacgttgacg aggagatgtt ccagcacgtg gacatattcg ggatattcca gacctacttc    660
aagagggaga tgagcgactt caagctcaag actgtagccc tcaaggtcct gggatccaag    720
gtgccacttg gcgccctgct ggatttcgag aggcctggtg acataaggaa gctcacggag    780
ttcttcgaga ggcgcaggga tctccttaga ctctacaaca tggatcagac acaggcgata    840
tggatgataa acagcgagtc aggtgtgctc cagacctaca tcacccaggc taggctcgct    900 aacataaatac cttggcaccg ggatctctcc gagaagcaga ttgctcacag gaagtatata    960
tcctacaaca agatcgtcga gaaccttgtc ttgaagaaag ctctatctca cagtccaagg   1020
atagttttcc catctaagaa gaacggtgag aacgaagact gggatgagga tgcaaaggag   1080
agcacataca ctggagcaat agtgttcaac ccgattccag gctatgggga gaatgttgtg   1140
ctcctggact tcgcttcgat gtaccctagg gttataatga cgttcaacat ctcatacgac   1200
acatggaccc ctagccccgg tgaaaacgac attcttgcgc cccacggtgg attcatcacc   1260 tccaggggagg ggttccttcc aacggtgcta agggagcttg aggggtacag gagtctagct   1320
aagaagatgg ttgacgcata tgagccaggc gaccccatga gggtcatatg gaacgccagg   1380
cagttcgcgt tcaaactcat actggttttcg gcttacggtg tagcaggatt caggcactct   1440
agactctaca gggttgagat agccgagagc atcacggggt acaccaggga cgccataatg   1500
aaggcgagag aggtgataga gaggcacggt tggagggtcc tctacgggga caccgacagc   1560
ctgttcttgt acaaccccaa gatctcaagc gtggagaagg ctgctgaggt tgcatcaagc   1620
gagcttctcc cagccataaa ctcctttata agagactacg tggtggagag atggagggtt   1680
ccgaggagca gggttgtgtt ggagttcaag gttgacaggg tgtactcgaa gctgaagctg   1740
ctgagtgtga agaagaggta ctacggcttg gttgcgtggg aggagaggat gcttgagcaa   1800
ccctacattc agatcaaggg ccttgaggct aggagggtg attggcctga cctggtgaag   1860
gagatacagt cagaggtgat caagctgtac ctcctggagg gacccatggc tgtagacagg   1920
tatctcaggg agatgaagag gaagctcctg tccggggaga taccctttgga gaagcttgtt   1980 atcaagaagc atctgaacaa gaggcttgac gagtataagc ataacgcgcc ccactacagg   2040
gctgcaaaga agctcctgga gatgaggttc ccggttagaa ctggggatag aatagagttc   2100
atataccttg acgacaaggt gatccccatg gttccaggac tgaagctatc agaggttgac   2160
ctgaagaagt ggtggaggaa atacgttgtc ccggtggtcg agagactgga gatagagagc   2220
agagggagct tgctggacag gtacctaggg tga                                  2253
```

<210> SEQ ID NO 16
<211> LENGTH: 750

-continued

```
<212> TYPE: PRT
<213> ORGANISM: Unknown
<220> FEATURE:
<223> OTHER INFORMATION: Uncultured newly isolated virus

<400> SEQUENCE: 16
```

| | | | | | | | | | | | | | | | |
|---|---|---|---|---|---|---|---|---|---|---|---|---|---|---|---|
| Met | Ser | Tyr | Phe | Val | Asp | Ser | Gly | Ala | Thr | Met | Leu | Lys | Leu | Ile | Leu |
| 1 | | | | 5 | | | | | 10 | | | | | 15 | |
| Arg | Gly | Ser | Gly | Gly | Lys | Lys | Val | Val | Thr | Val | Pro | Ala | Pro | Phe | Asn |
| | | | 20 | | | | | 25 | | | | | 30 | | |
| Pro | Tyr | Phe | Phe | Ile | Lys | Lys | Arg | Asp | Leu | Asp | Arg | Ala | Gln | Ser | Ile |
| | | | 35 | | | | 40 | | | | | 45 | | | |
| Leu | Pro | Val | Leu | Thr | Leu | Ser | Val | Glu | Asp | Ala | Asp | Ala | Ile | Thr | Ala |
| | 50 | | | | | 55 | | | | | 60 | | | | |
| Glu | Gly | Glu | Arg | Val | Val | Lys | Ile | Ser | Val | Pro | Thr | Pro | Pro | Leu | Val |
| 65 | | | | | 70 | | | | | 75 | | | | | 80 |
| Arg | Val | Val | Arg | Glu | Lys | Leu | His | Glu | Glu | Gly | Ile | Glu | Ser | Tyr | Glu |
| | | | | 85 | | | | | 90 | | | | | 95 | |
| Ala | Asp | Ile | Pro | Tyr | Thr | Arg | Arg | Val | Met | Ile | Asp | Leu | Asp | Leu | Lys |
| | | | 100 | | | | | 105 | | | | | 110 | | |
| Val | Ala | Tyr | Pro | Glu | Thr | Val | Ala | Ala | Phe | Asp | Ile | Glu | Val | Asp | Ala |
| | | | 115 | | | | | 120 | | | | | 125 | | |
| Thr | Arg | Gly | Phe | Pro | Asp | Ile | Asn | Asn | Pro | Gln | Ser | Arg | Val | Leu | Ser |
| | 130 | | | | | 135 | | | | | 140 | | | | |
| Ile | Ser | Val | Tyr | Asp | Gly | Ser | Glu | Glu | Ile | Phe | Leu | Cys | Ser | Asp | Asp |
| 145 | | | | | 150 | | | | | 155 | | | | | 160 |
| Glu | Ile | Glu | Met | Phe | Lys | Glu | Phe | Asn | Lys | Leu | Leu | Arg | Arg | Tyr | Asp |
| | | | | 165 | | | | | 170 | | | | | 175 | |
| Val | Leu | Ile | Gly | Trp | Asn | Ser | Ala | Ala | Phe | Asp | Tyr | Pro | Tyr | Leu | Val |
| | | | 180 | | | | | 185 | | | | | 190 | | |
| Glu | Arg | Ala | Lys | Val | Leu | Gly | Tyr | Tyr | Val | Asp | Glu | Glu | Met | Phe | Gln |
| | | | 195 | | | | | 200 | | | | | 205 | | |
| His | Val | Asp | Ile | Phe | Gly | Ile | Phe | Gln | Thr | Tyr | Phe | Lys | Arg | Glu | Met |
| | 210 | | | | | 215 | | | | | 220 | | | | |
| Ser | Asp | Phe | Lys | Leu | Lys | Thr | Val | Ala | Leu | Lys | Val | Leu | Gly | Ser | Lys |
| 225 | | | | | 230 | | | | | 235 | | | | | 240 |
| Val | Pro | Leu | Gly | Ala | Leu | Leu | Asp | Phe | Glu | Arg | Pro | Gly | Asp | Ile | Arg |
| | | | | 245 | | | | | 250 | | | | | 255 | |
| Lys | Leu | Thr | Glu | Phe | Phe | Glu | Arg | Arg | Arg | Asp | Leu | Leu | Arg | Leu | Tyr |
| | | | 260 | | | | | 265 | | | | | 270 | | |
| Asn | Met | Asp | Gln | Thr | Gln | Ala | Ile | Trp | Met | Ile | Asn | Ser | Glu | Ser | Gly |
| | | | 275 | | | | | 280 | | | | | 285 | | |
| Val | Leu | Gln | Thr | Tyr | Ile | Thr | Gln | Ala | Arg | Leu | Ala | Asn | Ile | Ile | Pro |
| | 290 | | | | | 295 | | | | | 300 | | | | |
| Trp | His | Arg | Asp | Leu | Ser | Glu | Lys | Gln | Ile | Ala | His | Arg | Lys | Tyr | Ile |
| 305 | | | | | 310 | | | | | 315 | | | | | 320 |
| Ser | Tyr | Asn | Lys | Ile | Val | Glu | Asn | Leu | Val | Leu | Lys | Lys | Ala | Leu | Ser |
| | | | | 325 | | | | | 330 | | | | | 335 | |
| His | Ser | Pro | Arg | Ile | Val | Phe | Pro | Ser | Lys | Lys | Asn | Gly | Glu | Asn | Glu |
| | | | 340 | | | | | 345 | | | | | 350 | | |
| Asp | Trp | Asp | Glu | Asp | Ala | Lys | Glu | Ser | Thr | Tyr | Thr | Gly | Ala | Ile | Val |
| | | | 355 | | | | | 360 | | | | | 365 | | |
| Phe | Asn | Pro | Ile | Pro | Gly | Leu | Trp | Glu | Asn | Val | Val | Leu | Leu | Asp | Phe |
| | 370 | | | | | 375 | | | | | 380 | | | | |
| Ala | Ser | Met | Tyr | Pro | Arg | Val | Ile | Met | Thr | Phe | Asn | Ile | Ser | Tyr | Asp |

```
             385                 390                 395                 400
Thr Trp Thr Pro Ser Pro Gly Glu Asn Asp Ile Leu Ala Pro His Gly
                405                 410                 415
Gly Phe Ile Thr Ser Arg Glu Gly Phe Leu Pro Thr Val Leu Arg Glu
                420                 425                 430
Leu Glu Gly Tyr Arg Ser Leu Ala Lys Lys Met Val Asp Ala Tyr Glu
                435                 440                 445
Pro Gly Asp Pro Met Arg Val Ile Trp Asn Ala Arg Gln Phe Ala Phe
            450                 455                 460
Lys Leu Ile Leu Val Ser Ala Tyr Gly Val Ala Gly Phe Arg His Ser
465                 470                 475                 480
Arg Leu Tyr Arg Val Glu Ile Ala Glu Ser Ile Thr Gly Tyr Thr Arg
                485                 490                 495
Asp Ala Ile Met Lys Ala Arg Glu Val Ile Glu Arg His Gly Trp Arg
                500                 505                 510
Val Leu Tyr Gly Asp Thr Asp Ser Leu Phe Leu Tyr Asn Pro Lys Ile
                515                 520                 525
Ser Ser Val Glu Lys Ala Ala Glu Val Ala Ser Ser Glu Leu Leu Pro
            530                 535                 540
Ala Ile Asn Ser Phe Ile Arg Asp Tyr Val Val Glu Arg Trp Arg Val
545                 550                 555                 560
Pro Arg Ser Arg Val Val Leu Glu Phe Lys Val Asp Arg Val Tyr Ser
                565                 570                 575
Lys Leu Lys Leu Leu Ser Val Lys Lys Arg Tyr Tyr Gly Leu Val Ala
                580                 585                 590
Trp Glu Glu Arg Met Leu Glu Gln Pro Tyr Ile Gln Ile Lys Gly Leu
                595                 600                 605
Glu Ala Arg Arg Gly Asp Trp Pro Asp Leu Val Lys Glu Ile Gln Ser
            610                 615                 620
Glu Val Ile Lys Leu Tyr Leu Glu Gly Pro Met Ala Val Asp Arg
625                 630                 635                 640
Tyr Leu Arg Glu Met Lys Arg Lys Leu Leu Ser Gly Glu Ile Pro Leu
                645                 650                 655
Glu Lys Leu Val Ile Lys Lys His Leu Asn Lys Arg Leu Asp Glu Tyr
                660                 665                 670
Lys His Asn Ala Pro His Tyr Arg Ala Ala Lys Lys Leu Leu Glu Met
            675                 680                 685
Arg Phe Pro Val Arg Thr Gly Asp Arg Ile Glu Phe Ile Tyr Leu Asp
            690                 695                 700
Asp Lys Val Ile Pro Met Val Pro Gly Leu Lys Leu Ser Glu Val Asp
705                 710                 715                 720
Leu Lys Lys Trp Trp Arg Lys Tyr Val Val Pro Val Glu Arg Leu
                725                 730                 735
Glu Ile Glu Ser Arg Gly Ser Leu Leu Asp Arg Tyr Leu Gly
                740                 745                 750

<210> SEQ ID NO 17
<211> LENGTH: 333
<212> TYPE: DNA
<213> ORGANISM: Unknown
<220> FEATURE:
<223> OTHER INFORMATION: Uncultured newly isolated virus

<400> SEQUENCE: 17
atgctcgtgc taagcactac ggagaagcta gtcctgttag ctgtcgtggt tgagacagag    60
```

```
tatggcaaga agccaaccac caaggggaag gtgtacagta ggtatacaga gctatcaagg      120
ttagctggag tggagcccgt gacaccaagg agaaccctcg atgtattgaa gaacctggct      180 gagaaggga tcctgtgggt caaggttgac agcttcggaa ggtatggtag gacgacggtt       240
gtcaaactac tagcaccccc aaccacccta tgccaggagc tagccgaaga tttgttgata      300
ggcgaggtgg cggaggaggt ctgcaggggg tga                                   333
```

<210> SEQ ID NO 18
<211> LENGTH: 110
<212> TYPE: PRT
<213> ORGANISM: Unknown
<220> FEATURE:
<223> OTHER INFORMATION: Uncultured newly isolated virus

<400> SEQUENCE: 18

```
Met Leu Val Leu Ser Thr Thr Glu Lys Leu Val Leu Ala Val Val
1               5                   10                  15

Val Glu Thr Glu Tyr Gly Lys Lys Pro Thr Thr Lys Gly Lys Val Tyr
            20                  25                  30

Ser Arg Tyr Thr Glu Leu Ser Arg Leu Ala Gly Val Glu Pro Val Thr
        35                  40                  45

Pro Arg Arg Thr Leu Asp Val Leu Lys Asn Leu Ala Glu Lys Gly Ile
    50                  55                  60

Leu Trp Val Lys Val Asp Ser Phe Gly Arg Tyr Gly Arg Thr Thr Val
65                  70                  75                  80

Val Lys Leu Leu Ala Pro Pro Thr Thr Leu Cys Gln Glu Leu Ala Glu
                85                  90                  95

Asp Leu Leu Ile Gly Glu Val Ala Glu Val Cys Arg Gly
            100                 105                 110
```

<210> SEQ ID NO 19
<211> LENGTH: 294
<212> TYPE: DNA
<213> ORGANISM: Unknown
<220> FEATURE:
<223> OTHER INFORMATION: Uncultured newly isolated virus

<400> SEQUENCE: 19

```
atgggagcgt gccctccact tactggtaag gtctacgcga gatacgctga gctcgcgagg      60
ctccacaagg tgaaacccat caccatgagg aggttgcagg acgtcctgaa gggcctagcg     120
aaggccggaa tactgagggt tgtggttcgc agcttcggca ggtacggtaa gacgtcgatc     180
atagtgttga ggcaaccacc gcaaaccctg tgcccaatac tcacagagga tctagtggta     240
ggggagatgg cggaggagat ctgcagagat acccagccca taccccccgg gtga           294
```

<210> SEQ ID NO 20
<211> LENGTH: 97
<212> TYPE: PRT
<213> ORGANISM: Unknown
<220> FEATURE:
<223> OTHER INFORMATION: Uncultured newly isolated virus

<400> SEQUENCE: 20

```
Met Gly Ala Cys Pro Pro Leu Thr Gly Lys Val Tyr Ala Arg Tyr Ala
1               5                   10                  15

Glu Leu Ala Arg Leu His Lys Val Lys Pro Ile Thr Met Arg Arg Leu
            20                  25                  30

Gln Asp Val Leu Lys Gly Leu Ala Lys Ala Gly Ile Leu Arg Val Val
        35                  40                  45
```

```
Val Arg Ser Phe Gly Arg Tyr Gly Lys Thr Ser Ile Ile Val Leu Arg
        50                  55                  60

Gln Pro Pro Gln Thr Leu Cys Pro Ile Leu Thr Glu Asp Leu Val Val
65                  70                  75                  80

Gly Glu Met Ala Glu Glu Ile Cys Arg Asp Thr Gln Pro Ile Pro Pro
                85                  90                  95

Gly

<210> SEQ ID NO 21
<211> LENGTH: 29
<212> TYPE: DNA
<213> ORGANISM: Artificial
<220> FEATURE:
<223> OTHER INFORMATION: Synthetic oligonucleotide

<400> SEQUENCE: 21
gagcagtatc agatacaagc ggccgcatc                                        29

<210> SEQ ID NO 22
<211> LENGTH: 28
<212> TYPE: DNA
<213> ORGANISM: Artificial
<220> FEATURE:
<223> OTHER INFORMATION: Synthetic oligonucleotide

<400> SEQUENCE: 22
tcgtcatagt ctatgttcgc cggcgtag                                         28

<210> SEQ ID NO 23
<211> LENGTH: 37
<212> TYPE: DNA
<213> ORGANISM: Artificial
<220> FEATURE:
<223> OTHER INFORMATION: Synthetic oligonucleotide

<400> SEQUENCE: 23
tgtctcagac agtcagactg ctgacagatg acttgca                               37

<210> SEQ ID NO 24
<211> LENGTH: 41
<212> TYPE: DNA
<213> ORGANISM: Artificial
<220> FEATURE:
<223> OTHER INFORMATION: Synthetic oligonucleotide

<400> SEQUENCE: 24
aacgtgcaag tcatctgtca gcagtctgac tgtctgagac a                          41

<210> SEQ ID NO 25
<211> LENGTH: 588
<212> TYPE: PRT
<213> ORGANISM: Artificial
<220> FEATURE:
<223> OTHER INFORMATION: Synthetic oligonucleotide

<400> SEQUENCE: 25

Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
                20                  25                  30

Asp Ser Ile Asp Glu Ile Pro Ala Lys Tyr Asn Glu Pro Val Tyr Phe
            35                  40                  45

Ala Leu Glu Thr Asp Glu Asp Arg Pro Val Leu Ala Ser Ile Tyr Gln
        50                  55                  60
```

```
Pro His Phe Glu Arg Lys Val Tyr Cys Leu Asn Leu Lys Glu Lys
65                  70                  75                  80

Val Ala Arg Phe Lys Asp Trp Leu Leu Lys Phe Ser Glu Ile Arg Gly
            85                  90                  95

Trp Gly Leu Asp Phe Asp Leu Arg Val Leu Gly Tyr Thr Tyr Glu Gln
            100                 105                 110

Leu Arg Asn Lys Lys Ile Val Asp Val Gln Leu Ala Ile Lys Val Gln
            115                 120                 125

His Tyr Glu Arg Phe Lys Gln Gly Gly Thr Lys Gly Glu Gly Phe Arg
        130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
            180                 185                 190

Leu Leu Tyr Glu Gln Leu Thr Ser Ser Thr Leu Asn Ser Leu Val Tyr
        195                 200                 205

Gln Leu Asp Gln Gln Ala Gln Lys Val Val Ile Glu Thr Ser Gln His
210                 215                 220

Gly Met Pro Val Lys Leu Lys Ala Leu Glu Glu Ile His Arg Leu
225                 230                 235                 240

Thr Gln Leu Arg Ser Glu Met Gln Lys Gln Ile Pro Phe Asn Tyr Asn
                245                 250                 255

Ser Pro Lys Gln Thr Ala Lys Phe Phe Gly Val Asn Ser Ser Ser Lys
            260                 265                 270

Asp Val Leu Met Asp Leu Ala Leu Gln Gly Asn Glu Met Ala Lys Lys
        275                 280                 285

Val Leu Glu Ala Arg Gln Ile Glu Lys Ser Leu Ala Phe Ala Lys Asp
290                 295                 300

Leu Tyr Asp Ile Ala Lys Arg Ser Gly Gly Arg Ile Tyr Gly Asn Phe
305                 310                 315                 320

Phe Thr Thr Thr Ala Pro Ser Gly Arg Met Ser Cys Ser Asp Ile Asn
                325                 330                 335

Leu Gln Gln Ile Pro Arg Arg Leu Arg Ser Phe Ile Gly Phe Asp Thr
            340                 345                 350

Glu Asp Lys Lys Leu Ile Thr Ala Asp Phe Pro Gln Ile Glu Leu Arg
        355                 360                 365

Leu Ala Gly Val Ile Trp Asn Glu Pro Lys Phe Ile Glu Ala Phe Arg
370                 375                 380

Gln Gly Ile Asp Leu His Lys Leu Thr Ala Ser Ile Leu Phe Asp Lys
385                 390                 395                 400

Asn Ile Glu Glu Val Ser Lys Glu Glu Arg Gln Ile Gly Lys Ser Ala
                405                 410                 415

Asn Phe Gly Leu Ile Tyr Gly Ile Ala Pro Lys Gly Phe Ala Glu Tyr
            420                 425                 430

Cys Ile Ala Asn Gly Ile Asn Met Thr Glu Glu Gln Ala Tyr Glu Ile
        435                 440                 445

Ser Gln Lys Val Glu Glu Val Leu His Lys Asp Cys Arg Gln His Gln
        450                 455                 460

Val Ala Tyr Glu Arg Phe Lys Tyr Asn Glu Tyr Val Asp Asn Glu Thr
465                 470                 475                 480

Trp Leu Asn Arg Thr Tyr Arg Ala Trp Lys Pro Gln Asp Leu Leu Asn
```

```
                        485                 490                 495
Tyr Gln Ile Gln Gly Ser Gly Ala Glu Leu Phe Lys Lys Ala Ile Val
            500                 505                 510

Leu Leu Lys Glu Thr Lys Pro Asp Leu Lys Ile Val Asn Leu Val His
        515                 520                 525

Asp Glu Ile Val Val Glu Ala Asp Ser Lys Glu Ala Gln Asp Leu Ala
        530                 535                 540

Lys Leu Ile Lys Glu Lys Met Glu Glu Ala Trp Asp Trp Cys Leu Glu
545                 550                 555                 560

Lys Ala Glu Glu Phe Gly Asn Arg Val Ala Lys Ile Lys Leu Glu Val
            565                 570                 575

Glu Glu Pro His Val Gly Asn Thr Trp Glu Lys Pro
        580                 585

<210> SEQ ID NO 26
<211> LENGTH: 588
<212> TYPE: PRT
<213> ORGANISM: Artificial
<220> FEATURE:
<223> OTHER INFORMATION: Synthetic oligonucleotide

<400> SEQUENCE: 26

Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
            20                  25                  30

Asp Ser Ile Asp Glu Ile Pro Ala Lys Tyr Asn Glu Pro Val Tyr Phe
        35                  40                  45

Asp Leu Ala Thr Asp Glu Asp Arg Pro Val Leu Ala Ser Ile Tyr Gln
    50                  55                  60

Pro His Phe Glu Arg Lys Val Tyr Cys Leu Asn Leu Leu Lys Glu Lys
65                  70                  75                  80

Val Ala Arg Phe Lys Asp Trp Leu Leu Lys Phe Ser Glu Ile Arg Gly
                85                  90                  95

Trp Gly Leu Asp Phe Asp Leu Arg Val Leu Gly Tyr Thr Tyr Glu Gln
            100                 105                 110

Leu Arg Asn Lys Lys Ile Val Asp Val Gln Leu Ala Ile Lys Val Gln
        115                 120                 125

His Tyr Glu Arg Phe Lys Gln Gly Gly Thr Lys Gly Glu Gly Phe Arg
    130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
            180                 185                 190

Leu Leu Tyr Glu Gln Leu Thr Ser Ser Thr Leu Asn Ser Leu Val Tyr
        195                 200                 205

Gln Leu Asp Gln Gln Ala Gln Lys Val Val Ile Glu Thr Ser Gln His
    210                 215                 220

Gly Met Pro Val Lys Leu Lys Ala Leu Glu Glu Ile His Arg Leu
225                 230                 235                 240

Thr Gln Leu Arg Ser Glu Met Gln Lys Gln Ile Pro Phe Asn Tyr Asn
                245                 250                 255

Ser Pro Lys Gln Thr Ala Lys Phe Phe Gly Val Asn Ser Ser Ser Lys
            260                 265                 270
```

-continued

```
Asp Val Leu Met Asp Leu Ala Leu Gln Gly Asn Glu Met Ala Lys Lys
            275                 280                 285

Val Leu Glu Ala Arg Gln Ile Glu Lys Ser Leu Ala Phe Ala Lys Asp
        290                 295                 300

Leu Tyr Asp Ile Ala Lys Arg Ser Gly Arg Ile Tyr Gly Asn Phe
305                 310                 315                 320

Phe Thr Thr Thr Ala Pro Ser Gly Arg Met Ser Cys Ser Asp Ile Asn
                325                 330                 335

Leu Gln Gln Ile Pro Arg Arg Leu Arg Ser Phe Ile Gly Phe Asp Thr
            340                 345                 350

Glu Asp Lys Lys Leu Ile Thr Ala Asp Phe Pro Gln Ile Glu Leu Arg
        355                 360                 365

Leu Ala Gly Val Ile Trp Asn Glu Pro Lys Phe Ile Glu Ala Phe Arg
    370                 375                 380

Gln Gly Ile Asp Leu His Lys Leu Thr Ala Ser Ile Leu Phe Asp Lys
385                 390                 395                 400

Asn Ile Glu Glu Val Ser Lys Glu Arg Gln Ile Gly Lys Ser Ala
                405                 410                 415

Asn Tyr Gly Leu Ile Tyr Gly Ile Ala Pro Lys Gly Phe Ala Glu Tyr
            420                 425                 430

Cys Ile Ala Asn Gly Ile Asn Met Thr Glu Glu Gln Ala Tyr Glu Ile
        435                 440                 445

Ser Gln Lys Val Glu Glu Val Leu His Lys Asp Cys Arg Gln His Gln
    450                 455                 460

Val Ala Tyr Glu Arg Phe Lys Tyr Asn Glu Tyr Val Asp Asn Glu Thr
465                 470                 475                 480

Trp Leu Asn Arg Thr Tyr Arg Ala Trp Lys Pro Gln Asp Leu Leu Asn
                485                 490                 495

Tyr Gln Ile Gln Gly Ser Gly Ala Glu Leu Phe Lys Lys Ala Ile Val
            500                 505                 510

Leu Leu Lys Glu Thr Lys Pro Asp Leu Lys Ile Val Asn Leu Val His
        515                 520                 525

Asp Glu Ile Val Val Glu Ala Asp Ser Lys Glu Ala Gln Asp Leu Ala
    530                 535                 540

Lys Leu Ile Lys Glu Lys Met Glu Glu Ala Trp Asp Trp Cys Leu Glu
545                 550                 555                 560

Lys Ala Glu Glu Phe Gly Asn Arg Val Ala Lys Ile Lys Leu Glu Val
                565                 570                 575

Glu Glu Pro His Val Gly Asn Thr Trp Glu Lys Pro
            580                 585
```

<210> SEQ ID NO 27
<211> LENGTH: 588
<212> TYPE: PRT
<213> ORGANISM: Artificial
<220> FEATURE:
<223> OTHER INFORMATION: Synthetic oligonucleotide

<400> SEQUENCE: 27

```
Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
            20                  25                  30

Asp Ser Ile Asp Glu Ile Pro Ala Lys Tyr Asn Glu Pro Val Tyr Phe
        35                  40                  45
```

```
Ala Leu Glu Thr Asp Glu Asp Arg Pro Val Leu Ala Ser Ile Tyr Gln
 50                  55                  60

Pro His Phe Glu Arg Lys Val Tyr Cys Leu Asn Leu Leu Lys Glu Lys
 65                  70                  75                  80

Val Ala Arg Phe Lys Asp Trp Leu Leu Lys Phe Ser Glu Ile Arg Gly
                 85                  90                  95

Trp Gly Leu Asp Phe Asp Leu Arg Val Leu Gly Tyr Thr Tyr Glu Gln
                100                 105                 110

Leu Arg Asn Lys Lys Ile Val Asp Val Gln Leu Ala Ile Lys Val Gln
            115                 120                 125

His Tyr Glu Arg Phe Lys Gln Gly Gly Thr Lys Gly Glu Gly Phe Arg
        130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
                180                 185                 190

Leu Leu Tyr Glu Gln Leu Thr Ser Ser Thr Leu Asn Ser Leu Val Tyr
            195                 200                 205

Gln Leu Asp Gln Gln Ala Gln Lys Val Val Ile Glu Thr Ser Gln His
        210                 215                 220

Gly Met Pro Val Lys Leu Lys Ala Leu Glu Glu Ile His Arg Leu
225                 230                 235                 240

Thr Gln Leu Arg Ser Glu Met Gln Lys Gln Ile Pro Phe Asn Tyr Asn
                245                 250                 255

Ser Pro Lys Gln Thr Ala Lys Phe Phe Gly Val Asn Ser Ser Ser Lys
                260                 265                 270

Asp Val Leu Met Asp Leu Ala Leu Gln Gly Asn Glu Met Ala Lys Lys
            275                 280                 285

Val Leu Glu Ala Arg Gln Ile Glu Lys Ser Leu Ala Phe Ala Lys Asp
        290                 295                 300

Leu Tyr Asp Ile Ala Lys Arg Ser Gly Gly Arg Ile Tyr Gly Asn Phe
305                 310                 315                 320

Phe Thr Thr Thr Ala Pro Ser Gly Arg Met Ser Cys Ser Asp Ile Asn
                325                 330                 335

Leu Gln Gln Ile Pro Arg Arg Leu Arg Ser Phe Ile Gly Phe Asp Thr
            340                 345                 350

Glu Asp Lys Lys Leu Ile Thr Ala Asp Phe Pro Gln Ile Glu Leu Arg
        355                 360                 365

Leu Ala Gly Val Ile Trp Asn Glu Pro Lys Phe Ile Glu Ala Phe Arg
370                 375                 380

Gln Gly Ile Asp Leu His Lys Leu Thr Ala Ser Ile Leu Phe Asp Lys
385                 390                 395                 400

Asn Ile Glu Glu Val Ser Lys Glu Glu Arg Gln Ile Gly Lys Ser Ala
                405                 410                 415

Asn Tyr Gly Leu Ile Tyr Gly Ile Ala Pro Lys Gly Phe Ala Glu Tyr
            420                 425                 430

Cys Ile Ala Asn Gly Ile Asn Met Thr Glu Glu Gln Ala Tyr Glu Ile
        435                 440                 445

Ser Gln Lys Val Glu Glu Val Leu His Lys Asp Cys Arg Gln His Gln
450                 455                 460

Val Ala Tyr Glu Arg Phe Lys Tyr Asn Glu Tyr Val Asp Asn Glu Thr
465                 470                 475                 480
```

```
Trp Leu Asn Arg Thr Tyr Arg Ala Trp Lys Pro Gln Asp Leu Leu Asn
            485                 490                 495

Tyr Gln Ile Gln Gly Ser Gly Ala Glu Leu Phe Lys Lys Ala Ile Val
            500                 505                 510

Leu Leu Lys Glu Thr Lys Pro Asp Leu Lys Ile Val Asn Leu Val His
            515                 520                 525

Asp Glu Ile Val Val Glu Ala Asp Ser Lys Glu Ala Gln Asp Leu Ala
            530                 535                 540

Lys Leu Ile Lys Glu Lys Met Glu Glu Ala Trp Asp Trp Cys Leu Glu
545                 550                 555                 560

Lys Ala Glu Glu Phe Gly Asn Arg Val Ala Lys Ile Lys Leu Glu Val
                565                 570                 575

Glu Glu Pro His Val Gly Asn Thr Trp Glu Lys Pro
            580                 585

<210> SEQ ID NO 28
<211> LENGTH: 43
<212> TYPE: DNA
<213> ORGANISM: Artificial
<220> FEATURE:
<223> OTHER INFORMATION: Synthetic oligonucleotide

<400> SEQUENCE: 28
gtctgaggcc ctcagtccag ttacgctgga gtctgaggct cgt                    43

<210> SEQ ID NO 29
<211> LENGTH: 44
<212> TYPE: DNA
<213> ORGANISM: Artificial
<220> FEATURE:
<223> OTHER INFORMATION: Synthetic oligonucleotide

<400> SEQUENCE: 29
ctgtgagggc cttcattaga aaaactcatc gagcatcaag tgaa                   44
```